(12) United States Patent
Pihl et al.

(10) Patent No.: US 11,442,117 B2
(45) Date of Patent: Sep. 13, 2022

(54) SYSTEMS, DEVICES, AND METHODS FOR ELECTROPORATION INDUCED BY MAGNETIC FIELDS

(71) Applicant: Sigma Genetics, Inc., Seattle, WA (US)

(72) Inventors: Christopher James Pihl, Seattle, WA (US); Matthew Rein Scholz, Seattle, WA (US); David Edwin Kirtley, Seattle, WA (US)

(73) Assignee: SIGMA GENETICS, INC., Seattle, WA (US)

( * ) Notice: Subject to any disclaimer, the term of this patent is extended or adjusted under 35 U.S.C. 154(b) by 70 days.

(21) Appl. No.: 16/722,520

(22) Filed: Dec. 20, 2019

(65) Prior Publication Data
US 2020/0379060 A1 Dec. 3, 2020

Related U.S. Application Data

(63) Continuation of application No. 16/407,378, filed on May 9, 2019, now abandoned, which is a continuation of application No. PCT/US2017/060941, filed on Nov. 9, 2017.

(60) Provisional application No. 62/419,912, filed on Nov. 9, 2016.

(51) Int. Cl.
G01R 33/00 (2006.01)
A61B 5/05 (2021.01)

(52) U.S. Cl.
CPC ............ G01R 33/0023 (2013.01); A61B 5/05 (2013.01)

(58) Field of Classification Search
CPC ................ G01R 33/0023; A61B 5/05; A61M 2037/0007; A61K 41/0023; A61N 1/40; C12N 15/87; C12N 13/00
USPC ......................................... 324/309, 307, 300
See application file for complete search history.

(56) References Cited

U.S. PATENT DOCUMENTS

| 3,265,939 A | 8/1966 | Rinderer |
| 4,970,154 A | 11/1990 | Chang |
| 6,132,419 A | 10/2000 | Hofmann |
| 6,686,147 B1 | 2/2004 | Scanlan et al. |

(Continued)

FOREIGN PATENT DOCUMENTS

| CN | 110423783 A | 11/2019 |
| CN | 113736646 A | 12/2021 |

(Continued)

OTHER PUBLICATIONS

International Search Report and Written Opinion dated Feb. 14, 2018 for International Application No. PCT/US2017/60941, 19 pages.

(Continued)

Primary Examiner — Giovanni Astacio-Oquendo
(74) Attorney, Agent, or Firm — Cooley LLP

(57) ABSTRACT

A system includes a control device and a magnetic device coupled to the control device. The magnetic device is configured to inductively couple to a treatment target including one or more cells exposed to an agent, and includes one or more magnetic coils. The control device and the magnetic device are collectively configured to generate and apply a transient magnetic field to the treatment target to induce an electric field and porate the one or more cells and to permit the agent to enter the one or more cells.

16 Claims, 13 Drawing Sheets

(56) References Cited

U.S. PATENT DOCUMENTS

| | | | |
|---|---|---|---|
| 10,408,641 B2 * | 9/2019 | Gaude | E21B 33/064 |
| 10,426,561 B1 * | 10/2019 | Kelly | B25J 11/00 |
| 11,018,528 B2 * | 5/2021 | Sugiyama | H02M 7/4807 |
| 11,079,211 B2 * | 8/2021 | Harrigan | G01B 7/281 |
| 2003/0092182 A1 | 5/2003 | Sakamoto et al. | |
| 2005/0153437 A1 | 7/2005 | Kishida et al. | |
| 2005/0181508 A1 | 8/2005 | Fredriksson et al. | |
| 2006/0121612 A1 | 6/2006 | Tajima et al. | |
| 2006/0269531 A1 | 11/2006 | Beebe et al. | |
| 2008/0075701 A1 | 3/2008 | Hong et al. | |
| 2009/0029407 A1 | 1/2009 | Gazit et al. | |
| 2009/0081750 A1 | 3/2009 | Ragsdale et al. | |
| 2009/0326436 A1 | 12/2009 | Rubinsky et al. | |
| 2010/0249488 A1 | 9/2010 | Kardos et al. | |
| 2011/0070156 A1 | 3/2011 | Govindan et al. | |
| 2012/0064594 A1 | 3/2012 | Van Bree et al. | |
| 2012/0268035 A1 * | 10/2012 | Stanley | H05B 47/185 315/307 |
| 2014/0273229 A1 | 9/2014 | Meacham et al. | |
| 2020/0306433 A1 * | 10/2020 | Heide | H02J 7/0047 |

FOREIGN PATENT DOCUMENTS

| | | |
|---|---|---|
| GB | 2 298 370 B | 7/1997 |
| TW | 200512295 A | 4/2005 |
| WO | WO 2007/018562 A2 | 2/2007 |
| WO | WO 2018/089690 A1 | 5/2018 |

OTHER PUBLICATIONS

Extended European Search Report dated Jan. 12, 2021 for European Application No. 17869392.5, 7 pages.

* cited by examiner

SYSTEMS, DEVICES, AND METHODS FOR ELECTROPORATION INDUCED BY MAGNETIC FIELDS

CROSS-REFERENCE TO RELATED APPLICATIONS

This application is a continuation of U.S. Utility Application No. 16/407,378, titled "SYSTEMS, APPARATUSES, AND METHODS FOR ELECROPORATION INDUCED BY MAGNETIC FIELDS", filed May 9, 2019, which is a continuation of International Application No. PCT/US2017/060941, titled "SYSTEMS, APPARATUSES, AND METHODS FOR ELECROPORATION INDUCED BY MAGNETIC FIELDS", filed Nov. 9, 2017, which claims priority to U.S. Provisional Application No. 62/419,912, titled "SYSTEMS, APPARATUSES, AND METHODS FOR ELECROPORATION INDUCED BY MAGNETIC FIELDS", filed Nov. 9, 2016, the entire disclosure of each of which is incorporated herein by reference.

BACKGROUND

The embodiments described herein relate generally to inducing poration in biological organelles, cells, and/or tissue using electric and/or ionic currents induced by magnetic fields, also sometimes termed "magnetoporation".

Reversible and irreversible electroporation can result in temporary or permanent modification of cell membrane permeability; however, effectiveness of reversible electroporation is plagued by the tradeoff between undesirable cell death and efficiency, which is exacerbated by the general electroporation setup requiring that the current must flow between the electrodes, and through the medium being treated. Other shortcomings can include field enhancement caused by the electrodes themselves, bubbles or other non-homogeneous geometries within the volume being treated, which lead to current concentrations resulting in arcing, cell death, irreversible poration, and low efficacy. Additionally, the presence of high salt concentrations, and/or impure nucleic acid preparations can instigate arcing, which misdirects the current from its intended path and leads to poor electorporation efficiency. In an in vivo setting, the electrodes must penetrate the skin and other tissue layer(s), resulting in an invasive and painful experience for a patient.

Accordingly, there is a need for improved apparatuses, devices, and methods of modifying cells that overcome of these problems.

SUMMARY

In some embodiments, a system includes a control device and a magnetic device. The magnetic device is coupled to the control device and is configured to magnetically couple to a treatment target including one or more cells exposed to an agent. The magnetic device includes one or more magnetic coils. The control device and the magnetic device are collectively configured to generate and apply a transient magnetic field to the treatment target to porate the one or more cells and to permit the agent to enter the one or more cells.

In some embodiments, a method includes exposing one or more cells in a treatment target to an agent, and applying a transient magnetic field to the treatment target to porate the one or more cells and to permit the agent to enter the one or more cells.

DETAILED DESCRIPTION

Figure 1:
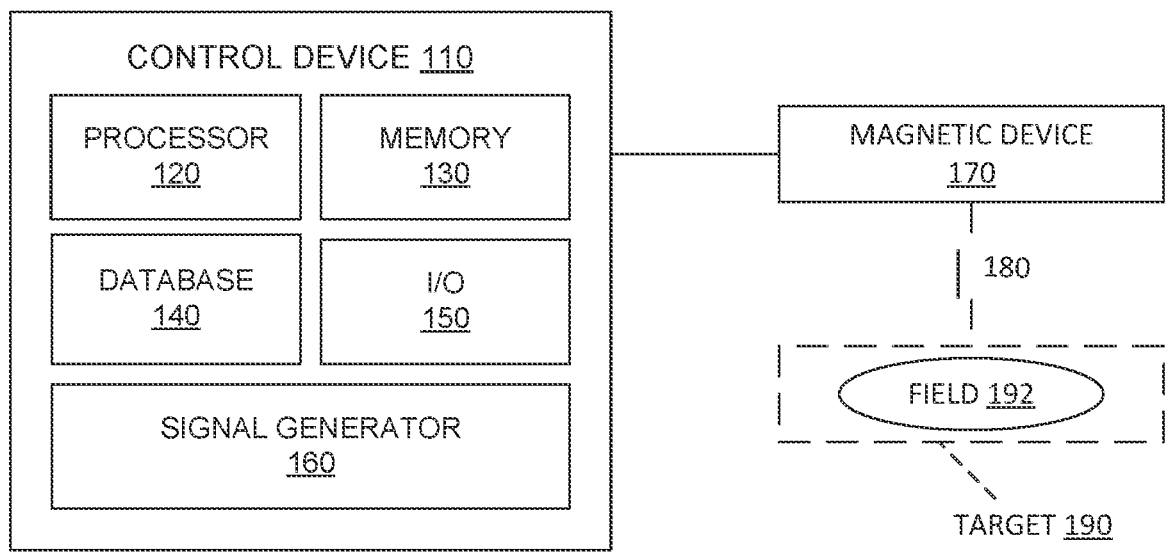
FIG. 1 is an illustration of a system for magnetoporation, according to embodiments.

In some aspects, the present disclosure provides methods of permeabilizing cells by exposing the cells to a current induced by a magnetic field, and introducing one or more exogenous agents (e.g. nucleic acids, drugs, polypeptides) into the permeabilized cell. The exogenous agents can be charged or uncharged. In some embodiments, the magnetic field allows exogenous agents to enter into the cell. In some embodiments, the magnetic field allows exogenous agents to actively diffuse into the cell, such as when, for example, when the exogenous agent is charged, such as a negatively charged DNA molecule. In some embodiments, the cells are removed from the subject before they are exposed to the magnetic field and exogenous agent. In some embodiments, the treated cells are then returned to the subject. In some embodiments, the magnetic field is applied to the subject or part of the subject in conjunction with administration of an exogenous agent.

Without being limited by any particular theory, generation of a transient magnetic field across a biological sample can result in the formation of a "secondary" conductive loop within the sample being treated, due to the inherently conductive nature of ionic biological fluids. There may be one or more rings of current and/or electric field created within the sample being treated. In some embodiments, the sample can be sufficiently conductive electrically to carry current, and/or been treated to be sufficiently conductive, with an ionic liquid, or ionic additive, such as, but not limited to a suitable buffer. In some cases, application of a transient magnetic field across a biological sample does not result in the induction of current and/or electric field within the sample sufficient to result in significant poration and/or transfection, but can still be employed to facilitate mechanical poration and/or transport of magnetic particles (e.g., ferrous particles, such as nanoparticles) for example, into the sample, such as a biological cell. In some embodiments, the induction of current and/or electric field can result in movement of the magnetic particles along field lines. In some embodiments, the particle(s) can carry, have attached/bonded thereto, and/or otherwise be associated with one or more agents that can be transported into the sample.

In some embodiments, a system includes a control device and a magnetic device coupled to the control device. The magnetic device is configured to magnetically couple to a treatment target including one or more cells exposed to an agent, the magnetic device including one or more magnetic coils. The control device and the magnetic device are collectively configured to generate and apply a transient magnetic field to the treatment target to porate the one or more cells and to permit the agent to enter the one or more cells. In some embodiments, the transient magnetic field is configured to induce an electric field in the treatment target to porate the one or more cells. In some embodiments, the transient magnetic field is configured to reversibly porate the one or more cells to permit the agent to enter the one or more cells. In some embodiments, the transient magnetic field defines a treatment volume of at least about 100 µL.

In some embodiments, the control device includes a set of independent circuits, the magnetic device is a first magnetic device of a set of magnetic devices, and each magnetic device of the set of magnetic devices including one or more magnetic coils. In such embodiments, the transient magnetic field is a first transient magnetic field of a set of transient magnetic fields and the control device and the set of magnetic devices are collectively configured to generate and apply the set of transient magnetic fields to the treatment target. In some embodiments, each magnetic device of the set of magnetic devices is independently addressable by a corresponding circuit of the set of independent circuits. In some embodiments, the magnetic device includes a ferromagnetic circuit element.

In some embodiments, the system includes a user interface configured to receive an indication of spatial information associated with application of the set of transient magnetic fields. The control device and the set of magnetic devices collectively configured to generate and apply the set of transient magnetic fields based on the indication of spatial information.

In some embodiments, the control device includes a signal generator configured to apply an electrical signal to the magnetic device. In some embodiments, the signal generator is selected from the group consisting of an oscillator, a frequency synthesizer, a sine-wave generator, a pulse generator, a random noise generator, an arbitrary waveform generator, and combinations thereof. In some embodiments, the electrical signal is selected from the group consisting of a pulsed ¼ sine wave, followed by an L/R decay, a sine wave, a decaying sine wave, a square wave, and an arbitrary waveform.

In some embodiments, the magnetic device includes a superconducting electromagnet configured to generate the transient magnetic field. In some embodiments, the one or more magnetic coils of the magnetic device are configured to encircle at least a portion of the treatment target during use. In some embodiments, the magnetic device includes one or more oscillating antennae. In some embodiments, each antenna of the one or more oscillating antennae is independently addressable.

In some embodiments, a method includes exposing one or more cells in a treatment target to an agent, and applying a transient magnetic field to the treatment target to porate the one or more cells and to permit the agent to enter the one or more cells. In some embodiments, the transient magnetic field is configured to induce an electric field in the treatment target to porate the one or more cells. In some embodiments, the transient magnetic field is a first transient magnetic field of a set of transient magnetic fields, and the applying further includes applying the set of transient magnetic fields to the treatment target. In some embodiments, the method further includes generating the transient magnetic field by applying an electrical signal to a magnetic device that is inductively coupled to the treatment target. In some embodiments, the electrical signal is selected from the group consisting of a pulsed ¼ sine wave followed by an L/R decay, a sine wave, a decaying sine wave, a square wave, and an arbitrary waveform. In some embodiments, the transient magnetic field defines a treatment volume of at least about 100 µL.

In some embodiments, the method further includes generating the transient magnetic field via a magnetic coil, and/or via a superconducting electromagnet. In some embodiments, the method further includes generating the transient magnetic field via a magnetic coil encircling at least a portion of the treatment target. In some embodiments, the method further includes generating the transient magnetic field via a set of magnetic coils. In some embodiments, each magnetic coil of the set of magnetic coils is independently addressable.

In some embodiments, the method further includes receiving an indication of spatial information associated with application of the set of transient magnetic fields, and the applying further includes applying the set of transient magnetic fields based on the indication of spatial information.

In some embodiments, the transient magnetic field is configured to reversibly porate the one or more cells to permit the agent to enter the one or more cells. In some embodiments, the method further includes reintroduced the one or more cells into the patient in an amount effective to treat a disease or disorder in the patient. In some embodiments, the patient is human. In some embodiments, the disease or disorder is an infection, a hereditary disorder, an environmentally-influenced disease or disorder, an autoimmune disease, or cancer.

In some embodiments, a system includes a control device and a magnetic device a magnetic device coupled to the control device, the magnetic device configured to inductively couple to a treatment target including one or more cells exposed to an agent. The magnetic device includes one or more magnetic coils. The control device and the magnetic device are collectively configured to generate and apply a transient magnetic field to the treatment target to induce an electric field in the treatment target and to permit the agent to enter the one or more cells.

In some embodiments, a system includes a control device including two or more circuits. The system also includes a set of magnetic devices coupled to the control device, each magnetic device of the set of magnetic devices configured to magnetically couple to the treatment target including one or more cells exposed to an agent. Each magnetic device of the set of magnetic devices includes two or more magnetic coils, each magnetic coil associated with a different circuit of the control device. In some embodiments, the control device and the set of magnetic devices collectively configured to generate and apply two or more transient magnetic fields to the treatment target to induce an electric field in the treatment target to permit the agent to enter the one or more cells.

In some embodiments, the treatment target includes one or more of a container, a medical device, and a mammalian target. In some embodiments, the one or more cells are in vitro, in vivo, or ex vivo. In some embodiments, the one or more cells are mammalian cells. In some embodiments, the mammalian cells are selected from the group consisting of heart cells, liver cells, kidney cells, skin cells, brain cells, bladder cells, testes cells, ovary cells, uterus cells, eye cells, pancreatic cells, fallopian tube cells, vaginal cells, teste cells, prostate cells, placenta cells, large intestine cells, small intestine cells, colon cells, cancer cells, muscle cells, epithelial cells, connective tissue cells, nerve cells, blood cells, white blood cells, red blood cells, T cells, B cells, lymphocytes, antigen presenting cells, platelets, macrophages, monocytes, granulocytes neutrophils, eosinophils, basophils, and cancer cells. In some embodiments, the one or more cells are bacterial cells, fungal cells, parasite cells, or plant cells.

In some embodiments, the agent is a nucleic acid. In some embodiments, the nucleic acid is selected from the group consisting of DNA, RNA, siRNA, shRNA, miRNA, mtDNA, and DNA/RNA hybrids. In some embodiments, the nucleic acid is associated with an exosome, a polypeptide, viral vector, or artificial chromosome. In some embodiments, the nucleic acid includes one or more genes, open reading frames, or fragments.

In some embodiments, the agent is a polypeptide, mutant polypeptide, or fragment thereof. In some embodiments, the nucleic acid encodes a polypeptide, mutant polypeptide, or fragment thereof. In some embodiments, the polypeptide is selected from the group consisting of an enzyme, a ligand, a receptor, a structural protein, and a fusion protein. In some embodiments, the polypeptide is Apolipoprotein A-1 Milano. In some embodiments, the polypeptide is an antigenic polypeptide. In some embodiments, the antigenic polypeptide is from a mammalian cell, a bacteria, virus, parasite, or fungus.

In some embodiments, the mammalian cell is a cancer cell. In some embodiments, the cancer cell antigenic peptide is associated with a hematologic malignancy or a solid tumor. In some embodiments, the cancer cell antigenic peptide is a tumor antigen or a tumor-associated antigen. In some embodiments, the polypeptide is selected from the group consisting of a ligand, an antigen-binding moiety, a receptor, a ligand-receptor fusion, antibody, and a fragment thereof. In some embodiments, the antibody or fragment thereof is selected from the group consisting of a monoclonal antibody, polyclonal antibody, chimeric antibody, humanized antibody, scFv, VL, VH, CL, CH1 domain, F(ab)2 fragment, a bivalent antibody, a Fd fragment, or a Fv fragment.

In some embodiments, the agent is a conjugated drug or molecule. In some embodiments, the conjugated drug or molecule is radioimmunotherapy (RIT), antibody-directed enzyme prodrug therapy (ADEPT) or an antibody-drug conjugate. In some embodiments, the agent is a drug. In some embodiments, the drug is a chemotherapeutic drug, pro-apoptotic drug, biologic drug, antibiotic, anti-fungal drug, ACE inhibitor, steroid, immunosuppressant, immunostimulant, immunomodulatory, anti-inflammatory, or an anti-fibrotic drug.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "a" or "an" and the phrase "one or more" may be used interchangeably.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. In general, the term "or" as used herein should be interpreted as exclusive when the context explicitly indicates exclusivity is intended (e.g., when "or" is used in conjunction with terms of exclusivity such as "one of," "only one of," etc.).

As used herein, the words "proximal" and "distal" refer to direction closer to and away from, respectively, an operator of the medical device. Thus, for example, the end of a catheter or delivery device contacting the patient's body would be the distal end of the medicament delivery device, while the end opposite the distal end (i.e., the end operated by the user) would be the proximal end of the catheter or delivery device.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" may be used interchangeably.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±1%, ±2%, ±3%, ±4%, ±5%, ±6%, ±7%, ±8%, ±9%, or ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "transient" when associated with a field or a current refers to that field/current having an amplitude that varies at some time point during existence of the field/current. Said another way, if "dB/dt" is used to represent variation in magnetic field amplitude over time, at some time point during existence of a transient magnetic field, the dB/dt for that field is non-zero. Similarly, if "dI/dt" is used to represent variation in electric current over time, at some time point during existence of the electric current, the dI/dt for that current is non-zero.

FIG. 1 illustrates a system 100 for magnetoporation, according to an embodiment. The system 100 includes a control device 110 coupled to a magnetic device 170. The magnetic device 170 is configured to be coupled to a treatment target 190 via magnetic field coupling 180. In some embodiments, the magnetic device 170 includes one or more magnetic coils. In some embodiments, the magnetic device 170 includes a set of magnetic coils. The set of magnetic coils can encompass multiple coils, as well as a single coil with multiple turns, such as for example, when each turn can be independently addressed and controlled by one or more circuits of the control device 110, as described in greater detail herein.

The control device 110 and/or the magnetic device 170 can be communicatively coupled to each other and/or other devices (not shown) via a network. The network can be any type of network that can operatively connect and enable data transmission. The network can be, for example, a wired network (an Ethernet, local area network (LAN), etc.), a wireless network (e.g., a wireless local area network (WLAN), a Wi-Fi network, etc.), or a combination of wired and wireless networks (e.g., the Internet, etc.).

As illustrated, the control device 110 can include at least a processor 120 and a memory 130. The control device 110 can also include a database 140. In some instances, the database 140 can include multiple databases. In some instances, part or the entirety of the database 140 can be external to the device, or external to the system. In some instances, the device can also include an I/O component 150 (e.g., a network interface, a keyboard, a touchscreen, and/or the like) configured for interfacing with a user of the control device, with another device such as the magnetic device 170, and/or the like.

In some instances, the processor 120 includes one or more modules and/or components. Each module/component executed by the processor can be any combination of hardware-based module/component (e.g., a field-programmable gate array (FPGA), an application specific integrated circuit (ASIC), a digital signal processor (DSP)), software-based module (e.g., a module of computer code stored in the memory and/or in the database, and/or executed at the processor), and/or a combination of hardware- and software-based modules. Each module/component executed by the processor is capable of performing one or more specific functions/operations as described herein. In some instances, the modules/components included and executed in the processor 120 can be, for example, a process, application, virtual machine, and/or some other hardware or software module/component. The processor can be any suitable processor configured to run and/or execute those modules/components. The processor 120 can be any suitable processing device configured to run and/or execute a set of instructions or code. For example, the processor can be a general purpose processor, a central processing unit (CPU), an accelerated processing unit (APU), a field-programmable gate array (FPGA), an application specific integrated circuit (ASIC), a digital signal processor (DSP), and/or the like.

The memory 130 can be, for example, a Random-Access Memory (RAM) (e.g., a dynamic RAM, a static RAM), a flash memory, a removable memory, and/or so forth. In some instances, instructions associated with performing the operations described herein can be stored within the memory and/or the database 140 and executed at the processor 120.

The control device 110 can be coupled to (not shown) or include (as illustrated in FIG. 1) a signal generator 160 configured to generated an electrical signal for application to the magnetic device 170. For example, when the magnetic device 170 includes an induction/magnetic coil (discussed later), the generated electrical signal can have characteristics that induce a time-varying magnetic field in the coil which, in turn, induces an electric field in the target 190. In some embodiments, the signal generator 160 can be of any suitable type including, but not limited to, an oscillator, a frequency synthesizer, a sine-wave generator, a pulse generator, a random noise generator, an arbitrary waveform generator, combinations thereof, and/or the like. In some embodiments, the signal generator 160 includes an arbitrary waveform generator coupled with a broadband RF amplifier. In some embodiments, the signal generator 160 includes an arbitrary waveform generator with a variable drive frequency, selectable waveforms, and/or auto-tune capability, to permit tuning based on the type of target/sample being treated. In some embodiments, the signal generator 160 includes a drive circuit operating at its natural resonant frequency. In some embodiments, the signal generator 160 can be configured to generate an electric signal as described herein upon receiving a trigger from a device external to the system 100. In some embodiments, the electrical signal can be characterized by simple pulsed current ¼ sine wave followed by an L/R decay, sine wave, decaying sine wave, square wave, defined arbitrary waveforms, or any waveform useful for electroporation.

The control device 110 is configured to transmit the electrical signal, or an indication thereof, to the magnetic device 170. The magnetic device 170 can include any suitable component(s) configured for generation of a time-varying magnetic field based on the electrical signal such as, for example, a resistive electromagnet (such as a solenoid), a superconducting electromagnet, and/or the like. In some embodiments, the magnetic device 170 can include multiple electromagnetic components, such as multiple coils (e.g., a yin-yang coil or Helmholtz type arrangement), for generating complex magnetic fields. In some embodiments, each electromagnetic component can be independently addressable, i.e., can be independent supplied a different electrical signal, or a different portion thereof, than another electromagnetic component of the magnetic device 170. Generally, the control device 110 and the magnetic device 170 can be collectively configured to generate and apply a transient magnetic field to the treatment target 190 to porate one or more cells and to permit an agent to enter the one or more cells. Without being bound by any theory in particular, in some embodiments, the transient magnetic field induces an electric field in the treatment target 190, and the electric field in turn affects the poration of the one or more cells.

In some embodiments, the magnetic device 170 can include a set of magnetic coils. In some embodiments, the set of magnetic coils can include a solenoid, where each turn of the solenoid being a different magnetic coil. In such embodiments, each turn/electromagnet/coil can be driven by a different circuit of the control device 110 (e.g., of the signal generator 160). For example, if the set of electromagnets includes a solenoid with five turns, the solenoid effectively functions as five single turn magnets, each associated with an individual driver circuit of the control device 110. Such embodiments having multiple magnets operating in parallel can result in reduced reactive impedance relative to the use of a single magnet/a single turn coil. Benefits of this approach permit increasing the dI/dt of the current in the circuit driving the magnetic device 180 and/or increasing the dB/dt of the magnetic field without resorting to higher voltages or other components. Additionally, by effectively decreasing the number of coil turns in the magnetic device, the effective ratio of turns (also sometimes referred to as the "turns ratio") between the magnetic device 170 and the treatment target 190 is increased relative to a single turn so that the loop voltage of the electric field induced in the treatment target is increased, thereby promoting the generation of electric fields with sufficient voltages useful for inducing poration and/or transfection. Furthermore, such arrangements also result in substantially uniform current density along the axial length of the coil, which permits substantially uniform treatment of the treatment target 170.

Another benefit of use of a multi-turn coil is the reduced effect of the reactive impedance of not only the coil itself, but also of the circuit that drives the coil. As an example, a for a single-turn coil with a reactive impedance of 10 nH, a driving circuit coupled to the coil with a reactive impedance of 20 nH (e.g., stray impedance), and a driving voltage of 1,000 V, the voltage that is delivered to the treatment target is the ratio of the coil impedance to that of the sum of the coil and circuit impedance. In this case, $\frac{1}{3}^{rd}$, or about 33%, or about 333 V is delivered to the treatment target. When the coil now includes five parallel turns, it still has an impedance of about 10 nH. Each individual drive circuit (five circuits overall) has the reactive impedance of 20 nH, but due to parallel operation, the overall impedance associated with the circuits as a parallel group is 20 nH divided by 5, or only about 4 nH. At the same operating voltage of 1,000 V, now $\frac{10}{14}^{th}$, or about 71%, or about 714 volts are delivered to the treatment target. Since the total impedance is reduced, the dB/dt of the generated magnetic field is also increased, which increases the applied electric field in the treatment target, increasing the likelihood of poration.

Figure 6A:
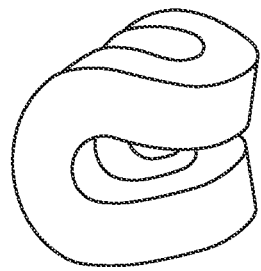
FIGS. 6A-6F illustrate example coils, according to embodiments.
Figure 6C:
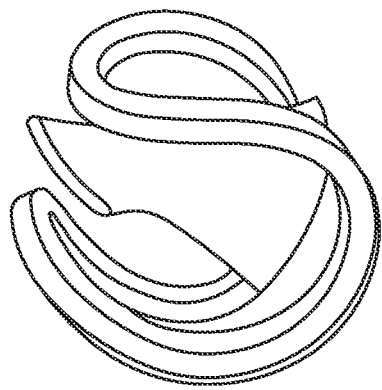
Figure 6B:
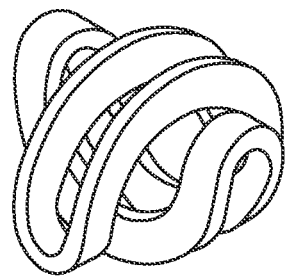
Figure 6D:
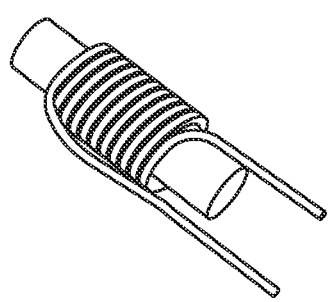
Figure 6E:
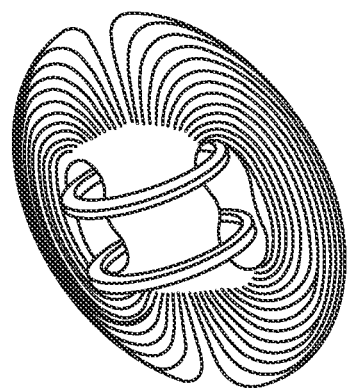

In some embodiments, the electrical signal includes a high voltage pulse followed by low voltage pulses. In this scenario, when a magnetic inductor/core is saturated, it will generate a transient pulse when it transitions between saturated and unsaturated states. In this manner, a high transient voltage can be created in the driving coil without the use of high voltage or complex circuitry. FIG. 6D illustrates an example solenoid on a rod type core. In some embodiments (not shown), the rod core extends beyond the solenoid and into the hollow center of the volume being treated. In this manner, the field can be coupled to the sample even without evoking saturation. The core could be any common geometry or material used in transformers such as e-cores, pot cores, rod cores, toroidal cores etc. In some embodiments, the volume being treated is about 50 µl or more, about 100 µl or more, about 1 ml or more, about 10 ml or more, about 100 ml or more, about 1 L or more, about 10 L or more, including all values and subranges in between.

Figure 6F:
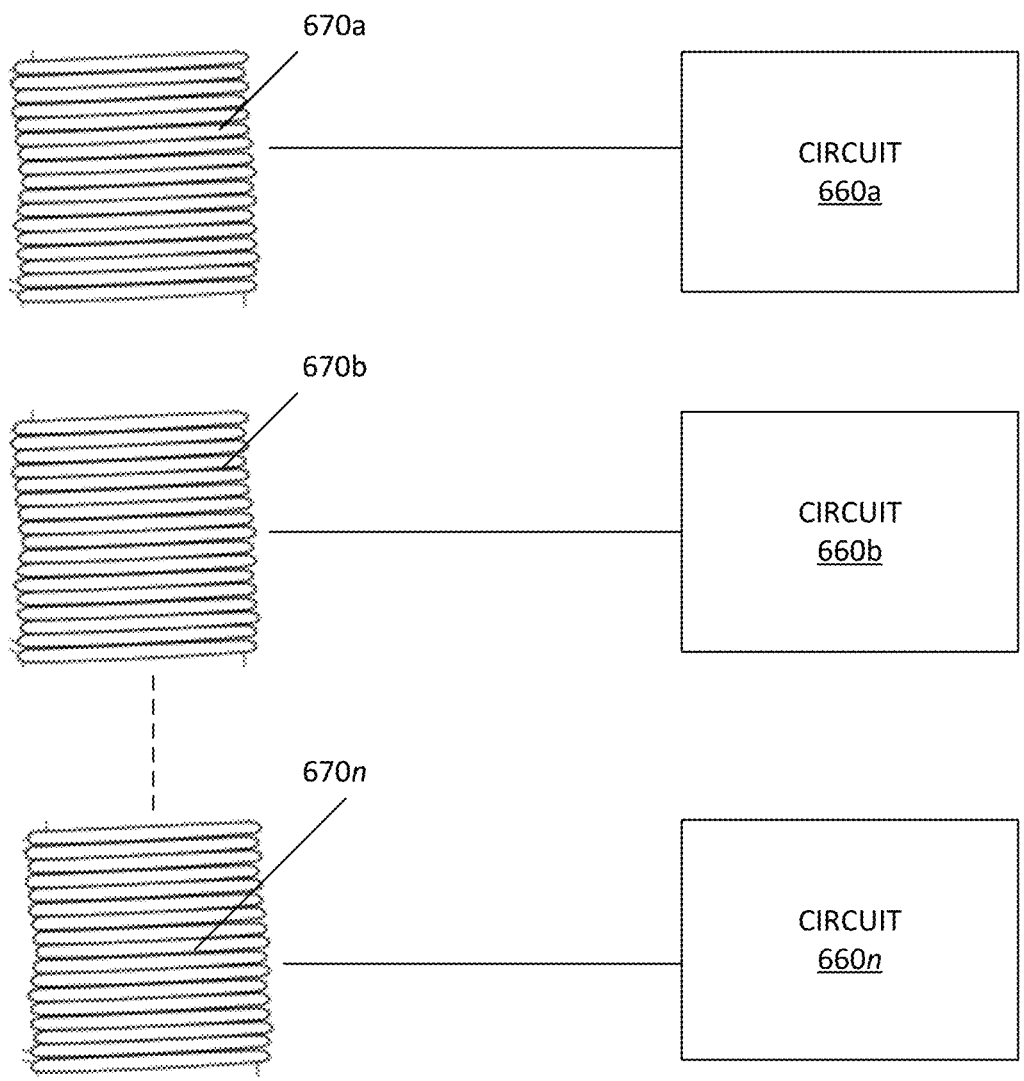

FIGS. 6A-6F illustrate various example coil geometries that can be employed with the systems, devices, and methods disclosed herein. FIG. 6F in particular illustrates the embodiments where multiple magnetic coils 670a-670n, of single or multiple turns of a single magnetic coil, are employed to generate the magnetic field 190, and each coil is associated with its own, independent driving circuit 660a-660n. In some embodiments, the magnetic device 170 includes suitable means to modify, concentrate, smooth, and/or otherwise control magnetic fields such as flux excluders/shapers/concentrators, and smoothing shells.

In such embodiments, a switching component/device (not shown) can be employed to selectively activate one or more of the multiple electromagnetic components. In some embodiments, the magnetic device 170 includes a core such as, for example, a ferromagnetic core. In some embodiments, the magnetic device 170 can include at least a processor and a memory.

As illustrated in FIG. 1, the magnetic device 170 can be configured to couple to the target 190 via the generated magnetic field 180. In some embodiments, the magnetic device 170, or a portion thereof, can be configured for physical coupling to the target 190 such via, for example, point contact, surface contact, probe, wrap-around (e.g., formed as a bracelet or a sleeve) contact, and/or the like.

The target 190 can be any suitable in vivo, ex vivo, and/or in vitro treatment target including, but not limited to, intracellular structures such as organelles, cells, tissues (including engineered tissue constructs), organs, anatomical parts such as limbs or the trunk section, and/or the like. In some embodiments (not shown), the treatment target can include and/or be associated with a holding medium such as, but not limited to, test tubes, culture plates/media, vacutainers, Eppendorf tubes, round bottom tubes, a scaffold, and/or the like. In some embodiments, the treatment target can include and/or be associated with a circulatory mechanism that periodically, continually, and/or intermittently circulates the target in and out of the magnetic field. For example, in some example embodiments, a patient's blood can be drawn into a container, treated by a coil/magnetic device would around the container, and transferred back into the patient such as during, for example, a cardiopulmonary bypass.

During use, when the transient magnetic field is applied to the target 190, a time-varying electric field 192 can be generated in at least a portion of the target 190. In some embodiments, the electric field 192 is such that it induces electroporation in the portion of the target. In some embodiments, the electric field 192 induces reversible electroporation. In some embodiments, the electric field 192 induces irreversible electroporation. In some embodiments, the electric field 192 can be characterized based on the nature of the target 190.

In some embodiments, the characteristics of the electric field 192 can be varied by controlling the voltage and current across a sample volume being treated. In some embodiments, voltage control can be accomplished by varying the frequency of the driving pulse from the signal generator 160, which can be characterized by the Maxwell-Faraday equation, describing the relationship of the voltage induced in a closed circuit (in this case the current loop inside the target 190) and the rate of change of the magnetic flux. Here, in the sample, the voltage across the electric field 192 is proportional to the rate of change of the applied magnetic field [dB/dt]. In some embodiments, other factors that can be accounted for can include the L/R decay rate of the target itself. This decay rate can be affected by both the geometry of the target 190, and the conductivity of the target.

In some embodiments, the magnetic field can define the electrical properties of a treatment volume based on the geometry of the treatment volume. For example, in the case of an induction coil, a treatment volume can be varied based on variations in the scale and/or geometry of the coil. Said another way, the coil can be relatively bigger or smaller in diameter, have a relatively greater or smaller number of windings, have a different cross-sectional shape, and/or the like.

In some embodiments, the system 100 can include an inductor (also sometimes referred to as a nonlinear inductor, a magnetic switch, and/or a saturable reactor) associated with the signal generator 160, the magnetic device 170, or both. In some embodiments, the inductor is associated with (e.g., is inline with) circuitry of the signal generator 160, or the magnetic device 170, or both. The use of an inductor in circuitry of the signal generator 160 can permit for generation of an electric signal/current in the circuit with a relatively higher dI/dt than that achieved without the use of the inductor. When this electric signal is applied to the magnetic device 170, the resulting magnetic field 192 can have a higher value of dB/dt than that achieved without the use of the inductor. The resulting increase in dI/dt and/or dB/dt can be beneficial for increasing likelihood and/or extent of poration observed in the treatment target. In some embodiments, the resulting increase in dI/dt and/or dB/dt can be beneficial for increasing likelihood and/or extent of transfection of the treatment target with an agent. In some embodiments, the desired level of dB/dt can be based on one or more factors, including, but not limited to, geometry of the treatment target 190, conductivity of the treatment target 190, the type/nature of the treatment target and/or of the cell(s) being treated, the agent to be transfected and/or transported into the cell(s), whether reversible or irreversible poration is desired, and/or the like. In some embodiments, the system 100 can include a user interface (e.g., a touch screen) to receive information related to one or more of these factors, and to generate the transient magnetic field based on the received information. For example, a user can input information related to the geometry of the treatment target, and the system 100 can be configured to select one or more magnetic coils of the magnetic device 170 for use in generating and applying multiple magnetic fields to the treatment target that overall conforms to the geometry of the treatment target.

In some embodiments, use of the inductor as described herein results in generation of a transient electric pulse every time the current in the circuit (e.g., of the signal generator 160) passes through zero. For example, if the circuit including the inductor is an oscillating ring-down circuit, a transient electric pulse is generated at every zero crossing of the current during ring-down, and results in a corresponding transient magnetic pulse in the generated magnetic field 192. As another example, if the circuit including the inductor is a continually driven circuit such as an H-bridge driven oscillator, a transient electric pulse is generated at every zero crossing as long as the circuit is driven, and results in a corresponding transient magnetic pulse in the generated magnetic field 192. In some embodiments, the inductor can be configured to provide a flyback voltage to the treatment target 190.

Figure 9A:
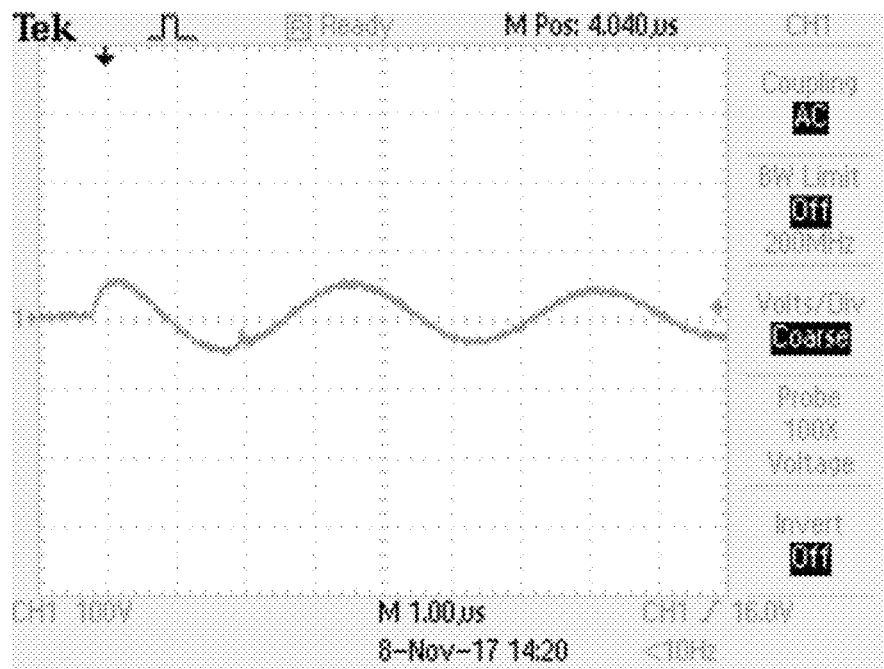
FIG. 9A illustrate an induced voltage waveform when no inductor is employed during application of a transient magnetic field of a sample.
Figure 9B:
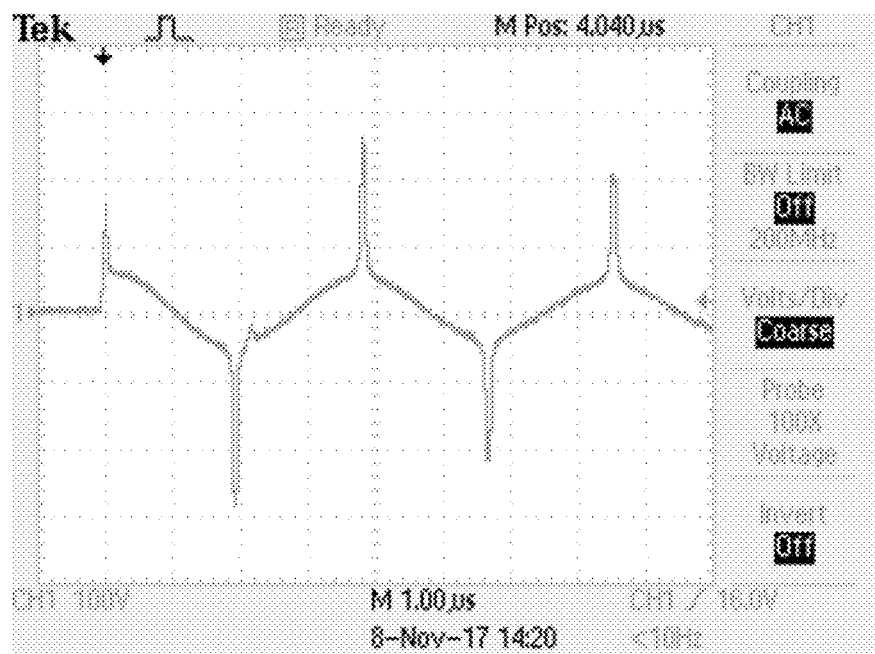
FIG. 9B illustrates an induced voltage waveform when an inductor is disposed in the same sample during application of a transient magnetic field.
Figure 10:
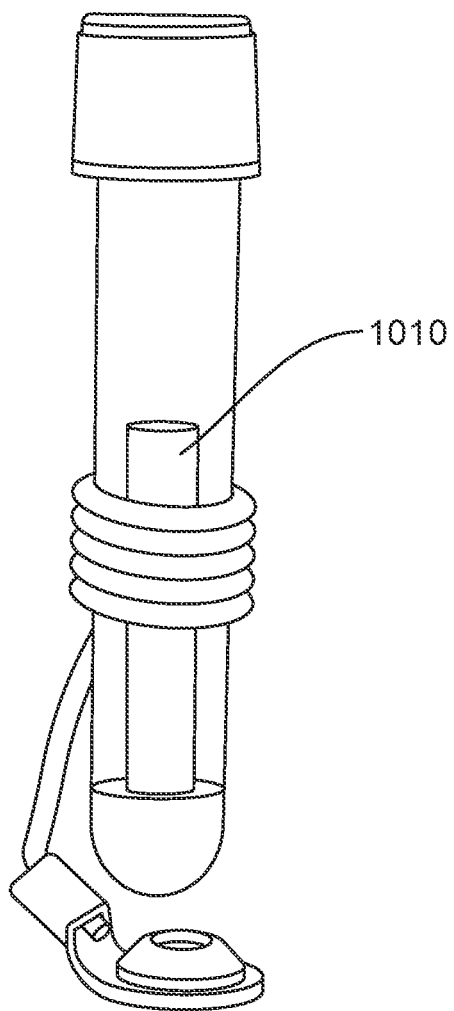
FIG. 10 illustrates an example setup including an inductor disposed inside a treatment target, according to some example embodiments.

FIGS. 9A-9B illustrate an example voltage waveform of an electric field having transient pulses induced due to placement of an inductor inside a treatment target/volume and being subject to a magnetic field, as illustrated in FIG. 10, where the rod-shaped inductor 1010 is positioned inside a test tube containing one or more cells. FIG. 9A illustrates the voltage waveform without the use of an inductor, and FIG. 9B illustrates the voltage waveform with use of an inductor. As seen in FIG. 9B, use of an inductor magnetic core in the sample results in sharp transients in the voltage waveform that are absent in FIG. 9A.

In some embodiments, such as in an in vitro setting, the inductor can be associated with and/or positioned within the treatment target 190. For example, the inductor can include a block of saturable magnetic material placed within a test tube containing one or more cells to be treated. In such embodiments, the inductor can be configured to affect the generation of a magnetic field having a higher dB/dt than that achieved without the use of the inductor. The inductor can be composed of any suitable saturable material including, but not limited to, iron, laminated steel, silicon steel, alloys such as mu-metal and permalloy, ferrites, powdered metals, ceramics, combinations thereof, and/or the like.

Figure 11:
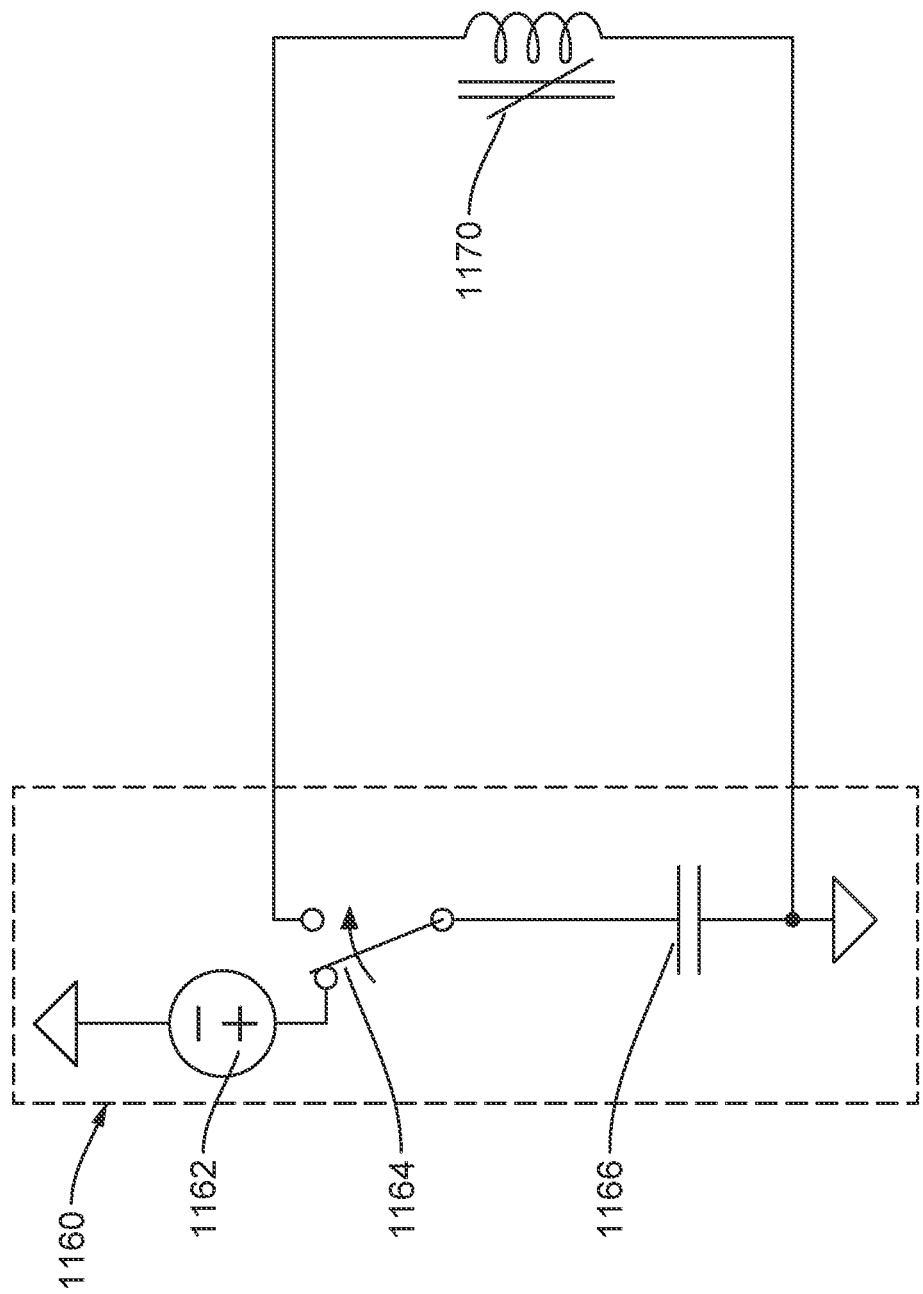
FIG. 11 is a circuit diagram illustrating a signal generator and a magnetic coil, according to some example embodiments.
Figure 12:
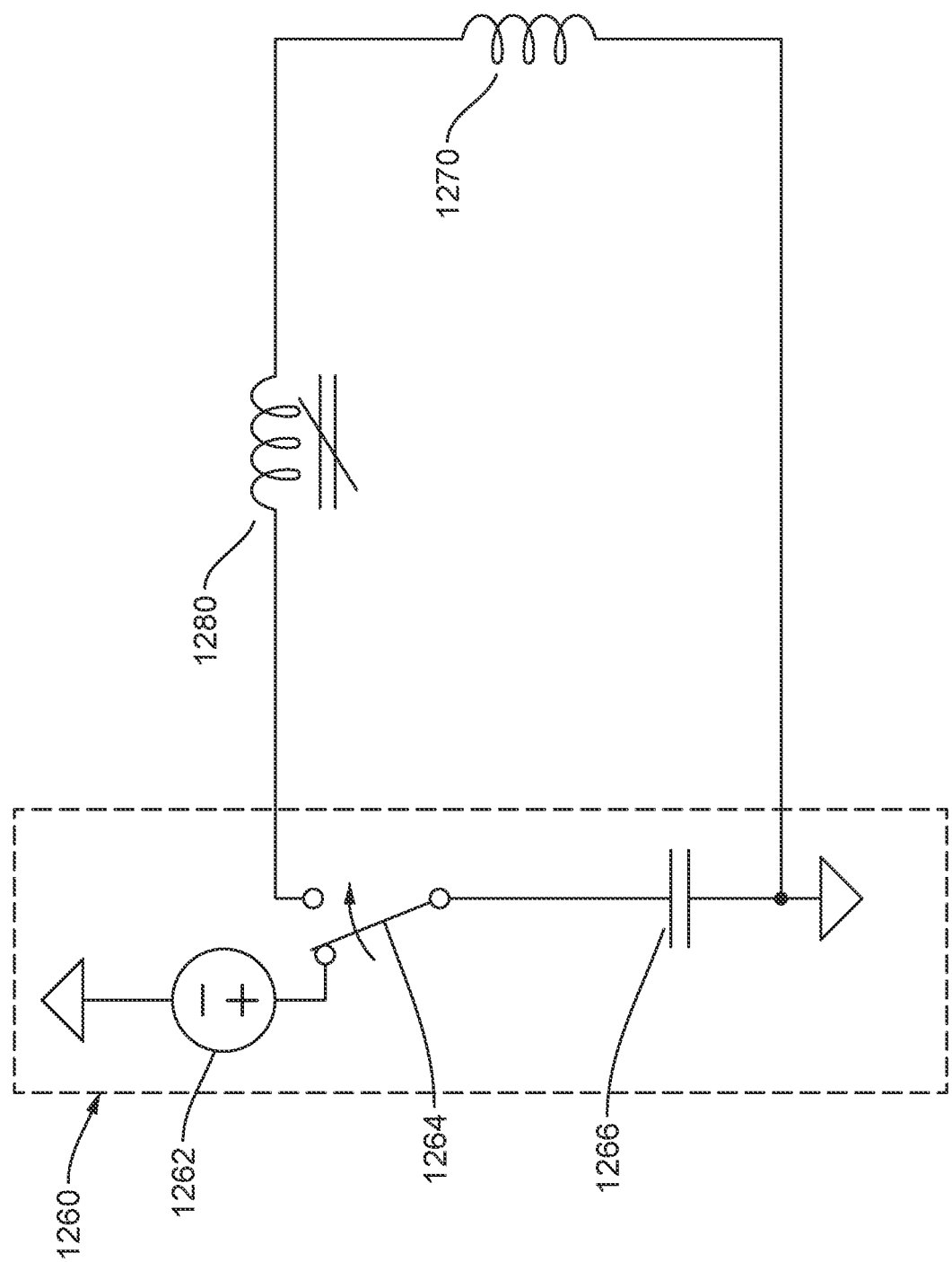
FIG. 12 is a circuit diagram illustrating an inductor disposed inline with a signal generator and a magnetic coil, according to some example embodiments.

FIG. 11 illustrates the instance where the magnetic core (not shown) is placed in the sample itself. The magnetic device 1170 is a magnetic coil used to couple the signal generator 1160 of the control device to the sample. The signal generator 1160 is illustrated as having a power source/battery 1162, a switch 1164, and a capacitor 1166. In an example embodiment, the power source 1162 can include a 4 kV battery/power supply, the capacitance of the capacitor 1166 is about 1.32 µF, and the coil 1170 has an inductance of about 250 nH. In contrast, FIG. 12 illustrates the instance where the inductor 1280 is placed in line with the magnetic device/coil 1270, and is electrically coupled to both the signal generator 1260 and the coil 1270. The signal generator 1260 is illustrated as having a power source/battery 1262, a switch 1264, and a capacitor 1266. In an example embodiment, the power source 1262 can include a 4 kV battery, the capacitance of the capacitor 1266 is about 1.32 µF, the coil 1270 has an inductance of about 250 nH, and the inductor 1280, also a coil in this example embodiment, has an inductance of about 10 nH.

FIGS. 2-6 illustrate various example use case scenarios for the system 100. It should be noted that unless explicitly stated otherwise, components in FIGS. 2-6 can be structurally and/or functionally similar to similarly named components in FIG. 1. For example, the magnetic device 270 can be similar to the magnetic device 170, and so on.

Figure 2:
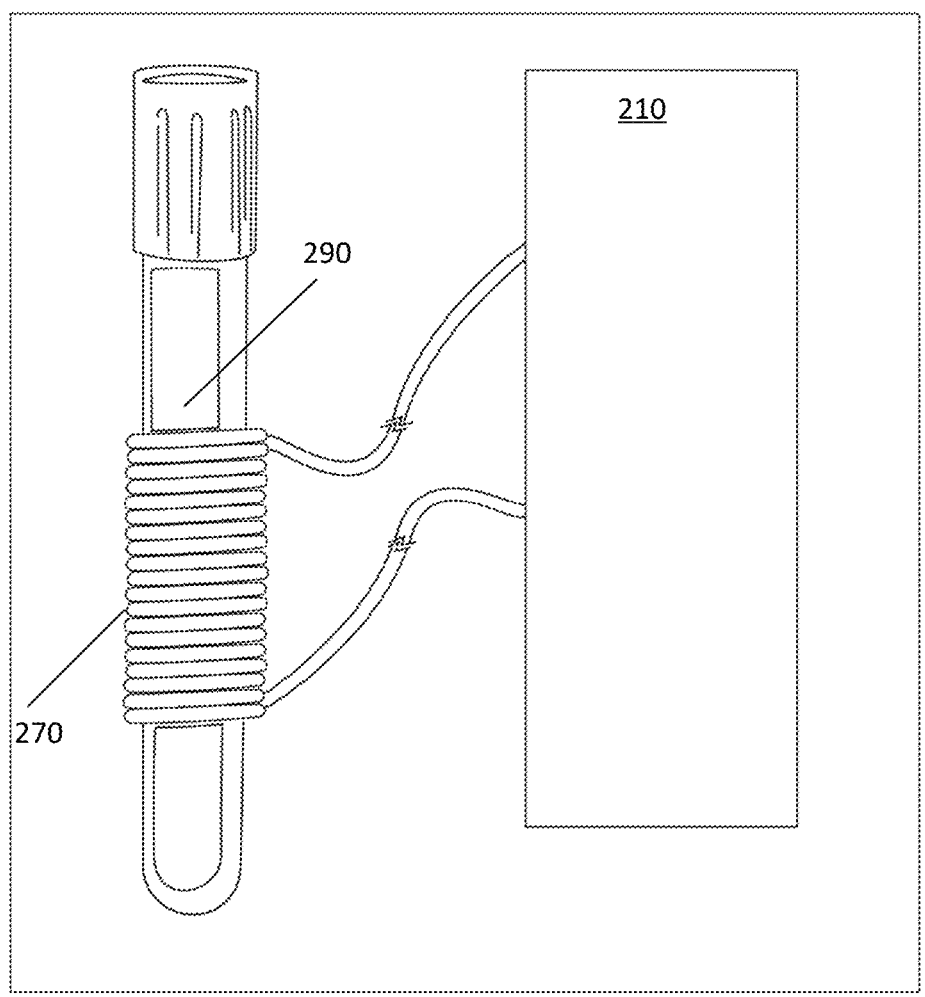
FIG. 2 is an example illustration of a system for magnetoporation, according to embodiments.

FIG. 2 illustrates a system 200 for magnetoporation, according to embodiments. The system 200 includes a control device 210 and a magnetic device 270 formed as a theta coil, though it is understood that the magnetic device 270 can be any suitable electromagnet, including a solenoid coil. The target 290 herein is a cell sample contained in a test tube container. The magnetic device 270 is proximal to the test tube, such that during use, an electric field is induced in the target 290, leading to reversible electroporation. When the cell culture media include agents such as DNA, RNA, therapeutic drugs, conductive particles capable of forming eddy currents upon application of a magnetic field (e.g., ferrous/electrically conductive particles/nanoparticles), and/or the like, the cell sample can effectively be transfected and/or otherwise treated with the agents without the direct application electric field and/or current.

Figure 3:
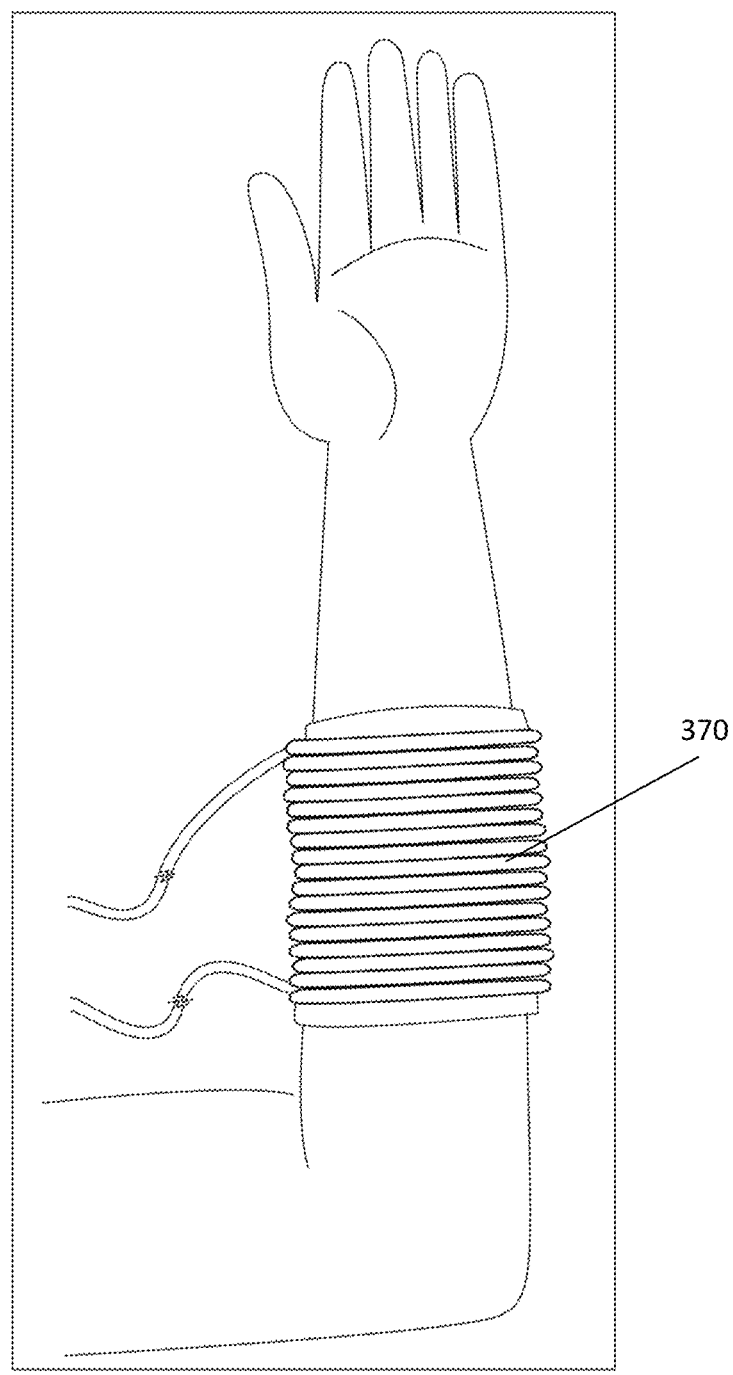
FIG. 3 is an example illustration of a magnetic device for magnetoporation during use, according to embodiments.

FIG. 3 illustrates a magnetic device 370 formed as a coil applied to an arm 390 as the target to treat one or more cells (e.g., skin cells, blood cells, muscle cells) and/or one or more tissue (e.g., skin, bone, muscle tissue) of the patient.

Figure 4:
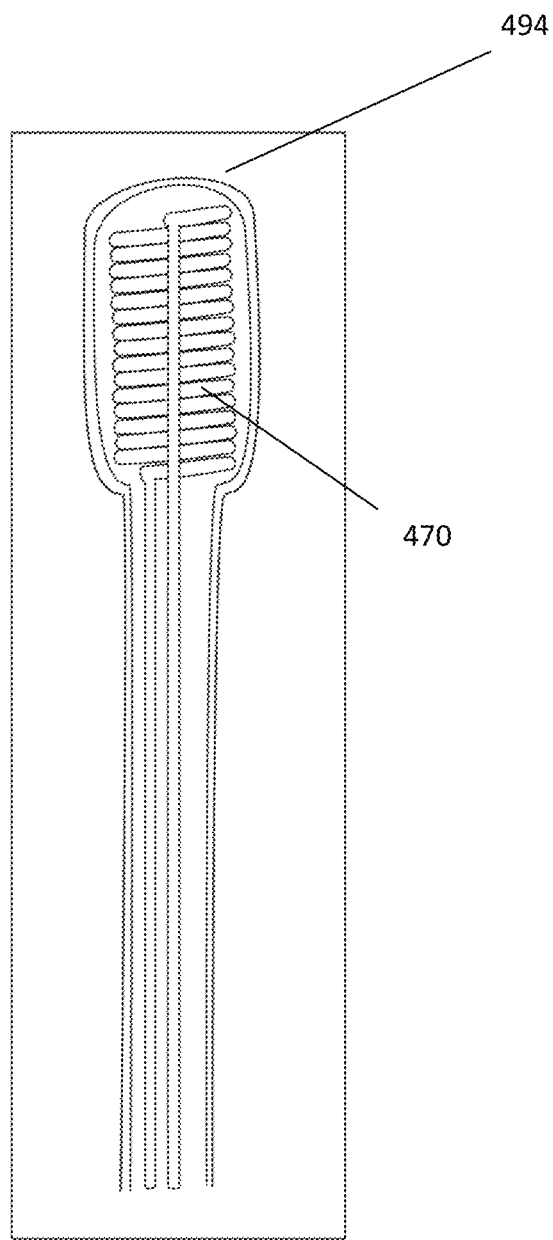
FIG. 4 is another example illustration of a magnetic device for magnetoporation during use, according to embodiments.

FIG. 4 illustrates a magnetic device 470 formed as an electromagnet/electromagnetic coil applied to a relatively distal end of a catheter 494 for in vivo delivery into a patient. In this manner, localized magnetoporation can be achieved in a target tissue, such as, for example, the GI tract. In some embodiments (not shown), the catheter 494 can include one or more infusion ports configured for delivery any suitable agent as disclosed herein to the target tissue. In some embodiments, the coil can be formed as a spirally wound coil, such as disclosed and illustrated in U.S. Pat. No. 3,998,081, the entire disclosure of which is incorporated herein by reference in its entirety.

Figure 5:
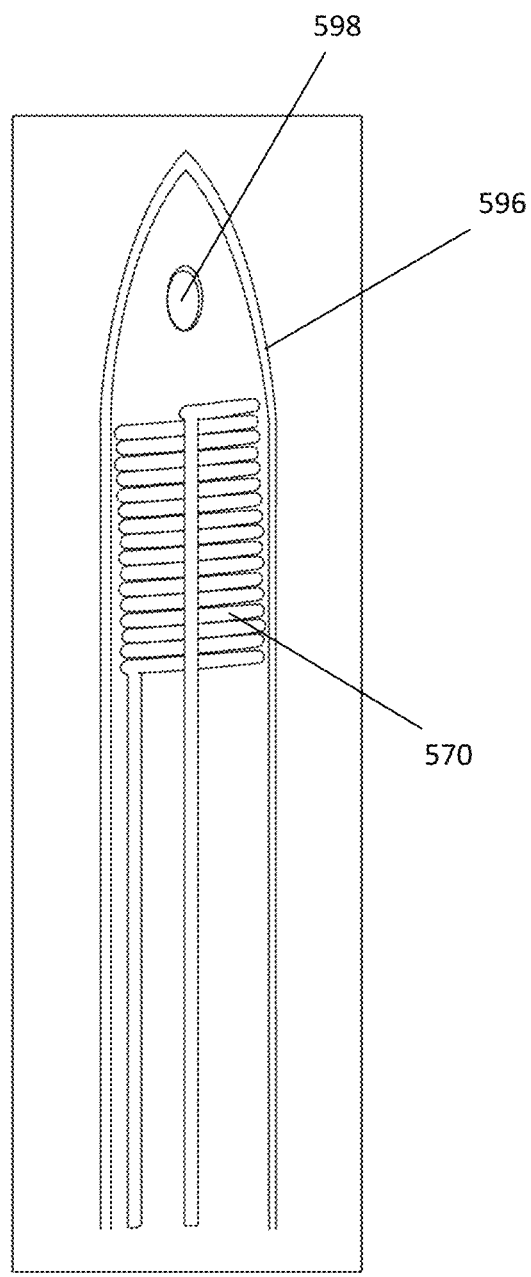
FIG. 5 is another example illustration of a magnetic device for magnetoporation during use, according to embodiments.

FIG. 5 illustrates a magnetic device 570 formed as a coil applied to a relatively distal end of a needle 596 for in vivo delivery into a patient. In some embodiments, the needle 596 can include one or more infusion ports 598 configured for delivery any suitable agent as disclosed herein to the target tissue. In some embodiments, the material of the needle 596 can be made of a suitable dielectric material to permit the magnetic field generated by the coil 570 to pass through to the target tissue. In this manner, localized magnetoporation can be achieved in a target tissue at depths accessible by typical needle lengths such as, for example, tumors, glands, bone marrow, and/or the like.

In some embodiments, the nature of application can guide the selection of geometry for the magnetic device. For example, for shallow/superficial in vivo applications, a patch-sized coil on the target area can be employed. For in vitro applications, embodiments discloses in FIGS. 2-5 can be employed. For large volume flow-through or batch applications, a geometry consisting of a sample container with a provision for a ferromagnetic core in the center of the container can be employed (e.g., see FIG. 2). In some embodiments, the center void of the sample container can be occupied by another solenoid. Since the degree of magnetic coupling and L/R ratios can drop precipitously as the coupled induced current wave travels inward radially from the surface, it is desirable to eliminate the center of the treated volume in order to keep the induced/applied/coupled effect uniform. The use of a solenoid in the center void effectively removes this volume, which can otherwise result in substantial deviation from achieving optimal or coupling. For some in vivo applications, such as drug delivery enhancement to tumors, or DNA/RNA delivery to deeper tissues, a needle like probe containing a driving coil as the magnetic device can be employed (e.g., see FIG. 5). For certain cancers such as colon and/or prostate cancers, a driving coil incorporated into an endoscope type assembly can be employed (e.g., see FIG. 4).

Magnetoporation possesses several advantages over traditional electroporation. Magnetoporation doesn't use electrodes, and can produce a substantially smooth field which induces a uniform current without the potential for a highly ionized path in the tissue. In some embodiments, a solenoid is used as the electromagnet to more reliably avoid current concentrations relative to when a theta coil is used. This field can be precisely controlled to maximize efficiency with minimal cell death. Magnetoporation can also result in less cell death in mixed cell populations.

Unlike electroporation, magnetoporation can be easily scaled with small or large volumes of material treated. Further, magnetoporation has superior current uniformity and distribution, better inherent arc suppression, no local field effects or field enhancements, has no limitations of batch size scalability, and importantly for biological and/or medical uses, no risk of contamination from electrodes. Moreover, the overall process can be subjected to much greater control and precision.

In vivo electroporation of skeletal muscle in humans and other large animals almost always requires multiple electrode needles (often an array of needles) which is very painful. In contrast, in vivo, magnetoporation should result in less cell death, and thus far less pain to the subject. Magnetoporation can also facilitate the targeting of skeletal muscle preferentially as opposed to skin. Skeletal muscle should be far better for in vivo protein production due to the relatively long life and robust protein production capacity of myocytes.

In some aspects, the present disclosure provides systems, devices, and methods of introducing one or more exogenous agents (e.g. nucleic acids, drugs, polypeptides) into cells by exposing the cell to a magnetic field. In some embodiments, the magnetic field creates pores in the cell membrane, allowing exogenous agents to passively diffuse into the cell. In some embodiments, the cells are removed from the subject before they are exposed to the magnetic field and exogenous agent. In some embodiments, the treated cells are then returned to the subject. In some embodiments, the magnetic field is applied to the subject or part of the subject in conjunction with administration of an exogenous agent to the subject. In some embodiments, the target is administered/exposed to the exogenous agent(s) prior to application of the magnetic field. In some embodiments, the target is administered/exposed to the exogenous agent(s) after application of the magnetic field. In some embodiments, the target is administered/exposed to the exogenous agent(s) during application of the magnetic field, i.e., there is at least some overlap between the timing of administration/exposure of the exogenous agent(s) and the application of the magnetic field.

Applications

In some aspects, the present disclosure provides systems, devices, and methods for use in any appropriate medical or biological application, including, but not limited to, treating infection, treating cancer, performing gene therapy, producing polypeptides, and/or treating or correcting hereditary disorders (e.g. cystic fibrosis, Down Syndrome, autoimmune diseases, muscular dystrophy, hemophilia, sickle cell anemia, etc.). In some embodiments, the present systems, devices, and methods are used ex vivo. In some embodiments, the present systems, devices, and methods are used in vivo.

The present systems, devices, and methods can be used in any appropriate subject, including but not limited to, mammalian, eukaryotic, insect, viral, vertebrate, fish, bird, prokaryotic, plant, fungi, and/or parasitic subjects. In some embodiments, the mammalian subject is livestock. In some embodiments, the mammalian subject is bovine, porcine, chicken, or fish. In some embodiments, the mammalian subject is human.

In some embodiments, the present systems, devices, and methods are used for vaccination-like applications. In some embodiments, these vaccination-like applications have the benefits of a DNA vaccine with less risk than an in vivo approach and no cell culture. For example, blood can be drawn, modified as whole blood, and immediately returned to the body. Further, RNA can be used to eliminate the risk of integration.

In some embodiments, the vaccine-like applications involve introducing an exogenous agent into an immune cell. In some embodiments, the immune cell is a B cell, a T cell, or an antigen-presenting cell (APC). In some embodiments, the exogenous agent introduced into the immune cell is a construct expressing an antigen. In some embodiments, the antigen is one that is targeted by the immune system. In some embodiments, the exogenous agent introduced into the immune cell is a construct expressing an antibody or fragment thereof that binds an antigen. In some embodiments, the exogenous agent introduced into the immune cell is a construct expressing an immunomodulatory agent. In some embodiments, the immunomodulatory agent is a small molecule, a nutraceutical, or a biologic.

In some embodiments, the present systems, devices, and methods are used for protein production. In some embodiments, the present methods are used for ex vivo protein production. In some embodiments, the ex vivo protein production involves practicing the disclosed systems, devices, and methods on cells in cell or tissue culture to express a particular protein and harvesting that protein for administration to a subject. In some embodiments, the present systems, devices, and methods are used for in vitro protein production, In some embodiments, the in vivo protein production involves practicing the disclosed systems, devices, and methods on mammalian tissue culture cells (e.g. CHO cells). In some embodiments, the in vivo protein production involves practicing the disclosed systems, devices, and methods on bacterial cells (e.g. *E. coli*).

In some embodiments, this ex vivo protein production has the same benefits as vaccination-like applications, but can avoid eliciting an immune response. In some embodiments, the ex vivo protein production takes advantage of the natural migratory characteristics of the target cell population. For example, in some embodiments, the target cell population is a macrophage. In some embodiments, the macrophage is loaded with a construct that makes a bacterial enzyme. In some embodiments, the bacterial enzyme is capable of breaking down 7-ketocholesterol (7KC) and the altered macrophage is used to clear a subject's arteries of oxidized cholesterol that can poison macrophages and result in arterial plague. For example, in some embodiments, the ex vivo protein production is used to alter the trafficking of cells. In some embodiments, the ex vivo protein production is used to alter the trafficking of exosomes. In some embodiments, the ex vivo protein production is used to alter the trafficking of exosomes by introducing siRNA into small targeted cell-producing liposomes to go across the blood brain barrier. In some embodiments, the target cell is an immune cell. In some embodiments, the immune cell is a B cell that is altered to express a chemokine and/or surface receptor that guides the altered B cell across the blood-brain barrier to deliver therapeutic proteins.

In some embodiments, the present systems, devices, and methods are used for porating cells. In some embodiments, the porated cells are blood cells. In some embodiments, the porated cells are red blood cells. In some embodiments, poration of red blood cells is useful for example for transport across the blood brain barrier.

In some embodiments, the present systems, devices, and methods are used for genome engineering. In some embodiments, the present disclosure provides methods for genome engineering that cause less tissue damage and inflammation than electroporation. In some embodiments, the present disclosure provides methods for genome engineering that are superior to methods using adeno-associated virus (AAV) (e.g. less chance of immune targeting of the virus itself). In some embodiments, the present methods are used for genome engineering over large areas, and thus can be used to enhance otherwise targeted technologies (e.g. CRISPR, gene therapy, etc.). For example, in some embodiments, the present methods are used to deliver a CRISPR construct to deliver a correct dystrophin gene. In some embodiments, the present methods are used to introduce DNA into muscle cells throughout the subject's body. In some embodiments, the present methods target other tissues (e.g. by varying the field and/or controlling the delivery of the construct).

In some embodiments, the present systems, devices, and methods are used for immunotherapy. In some embodiments, the immunotherapy is cancer immunotherapy. In some embodiments, the present methods are used to introduce exogenous agents into tumor cells. In some embodiments, the exogenous agent is a construct that expresses one or more proteins recognized by the immune system. In some embodiments, the exogenous agent is a construct that expresses one or more proteins that disrupt the tumor cell's natural immunomodulatory environment. In some embodiments, the present methods are used to induce apoptosis in a tumor cell. In some embodiments, the present methods are used to introduce an exogenous agent that induces apoptosis in a tumor cell.

In some embodiments, the present systems, devices, and methods are used to alter cells that are not endogenous to the subject. In some embodiments, the non-endogenous cells are eukaryotic. In some embodiments, the non-endogenous cells are prokaryotic. In some embodiments, the non-endogenous cells are mammalian cells (e.g. CHO cells or other tissue culture cells), yeast, bacteria, parasites, or another infection-causing cell.

In some embodiments, the present systems, devices, and methods are used in agriculture. In some embodiments, the present methods are used to alter crops. In some embodiments, the present methods are used to alter plant cells. In some embodiments, the crop is corn, soy, wheat, flax, cotton, or other agricultural plant.

Cell Types

In some aspects, the present disclosure provides for systems, devices, and methods of introducing exogenous agents and/or increasing cell permeabilization in any appropriate cell or tissue type. In some embodiments, the cell or tissue type includes, but is not limited to, mammalian, eukaryotic, insect, viral, vertebrate, fish, bird, prokaryotic, plant, fungi, parasitic, fetal, stem cell, tissue culture (e.g. CHO cells), and/or embryonic stem cell. In some embodiments, the cell is from a mammalian subject. In some embodiments, the mammalian subject is human. In some embodiments, the cell is autologous. In some embodiments, the cell is semi-autologous. In some embodiments, the cell is heterologous.

In some embodiments, the tissue is an organ. In some embodiments, the organ includes but is not limited to, heart, liver, kidney, skin, brain, bladder, testes, ovary, uterus, eye, pancreas, fallopian tubes, vagina, testes, prostate, placenta, large intestine, small intestine, colon, and/or stomach. In some embodiments, one or more cells is taken from an organ and treated ex vivo. In some embodiments, the organ is treated in vivo. In some embodiments, the organ is healthy. In some embodiments, the organ is diseased.

In some embodiments, the tissue is muscle, epithelial, connective, nervous, and/or blood. In some embodiments, the blood is whole blood. In some embodiments, the blood is a component of whole blood (e.g. red blood cells, white blood cells, platelets, etc.). In some embodiments, the blood is one or more blood cell types including, but not limited to, B cells, T cells, macrophages, lymphocytes, monocytes, granulocytes, neutrophils, eosinophils, and/or basophils. In some embodiments, one or more cells is taken from a tissue and treated ex vivo. In some embodiments, the tissue is treated in vivo. In some embodiments, the tissue is healthy. In some embodiments, the tissue is diseased.

In some embodiments, the present systems, devices, and methods are used to introduce one or more exogenous agents into and/or increasing cell permeabilization in one or more cancer or tumor cells. A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this disclosure are benign and malignant cancers, as well as dormant tumors or micrometastatses. Cancers which migrate from their original location and seed vital organs can eventually lead to the death of the subject through the functional deterioration of the affected organs.

In various embodiments, the systems, devices, and methods of the present disclosure are applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

In some embodiments, the cancer includes, but is not limited to, acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sezary syndrome, skin cancer (e.g. nonmelanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenstrom macroglobulinemia, and Wilms tumor.

In some embodiments, the cell is a bacterial cell including, but not limited to, *Bordetella, Bordetella, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and/or *Yersinia* genus. Cells from species of bacteria for use with the presently disclosed methods include, but are not limited to, *Bacillus anthracis*, Cutaneous anthrax, Pulmonary anthrax, Gastrointestinal anthrax, *Borrelia burgdorferi, Brucella abortus, Brucella canis, Brucella melitensis, Brucella suis, Campylobacter jejuni, Chlamydia trachomatis, Chlamydophila psittaci, Clostridium botulinum, Clostridium difficile, Clostridium perfringens, Clostridium tetani, Corynebacterium diphtheriae,* Nosocomial infections, Enteropathogenic *E. coli, Haemophilus influenzae, Helicobacter pylori, Legionella pneumophila, Listeria monocytogenes, Mycobacterium leprae, Mycoplasma pneumoniae, Neisseria gonorrhoeae, Neisseria meningitidis, Pseudomonas aeruginosa, Rickettsia rickettsii, Salmonella typhi, Salmonella typhimurium, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and/or *Yersinia pestis.*

In some embodiments, the cell is a fungal cell including, but not limited to, *Aspergillus, Blastomyces dermatitidis, Candida, Candida albicans, Coccidioides, C. neoformans, C. gattii, Histoplasma capsulatum,* Mucoromycotina, *Pneumocystis jirovecii, Sporothrix schenckii, Exserohilum, Cladosporium,* and/or *Cryptococcus.*

In some embodiments, the cell is a parasitic cell including, but not limited to, *Acanthamoeba, Anisakis, Ascaris lumbricoides,* Botfly, *Balantidium* coi, Bedbug, Cestoda, Chiggers, *Cochliomyia hominivorax, Entamoeba histolytica, Fasciola hepatica, Giardia lamblia,* Hookworm, *Leishmania, Linguatula serrata,* Liver fluke, *Loa loa, Paragonimus*—lung fluke, Pinworm, *Plasmodium falciparum,*

*Plasmodium malariae, Plasmodium vivax, Plasmodium knowlesi, Schistosoma, Strongyloides stercoralis,* Tapeworm, *Toxoplasma gondii, Trypanosoma,* Whipworm, and/or *Wuchereria bancrofti.*

In some embodiments, the cell is a plant cell taken from a crop including, but not limited to, corn, cotton, fruit trees and plants, nut trees and plants, rice, soybeans, oil crops, sugar, vegetable plants, wheat, and/or flax.

Exogenous Agents

Any appropriate exogenous agent can be introduced into a cell using the systems, devices, and methods of the present disclosure. These include, but are not limited to, drugs, nucleic acids, plasmids, linear sequences, conjugated molecules, polypeptides, nanoparticles, pro-drugs, vitamins, and/or small molecules.

In some embodiments, the systems, devices, and methods of the present disclosure introduce nucleic acids into one or more cells. Nucleic acids that may be used include but are not limited to, DNA, RNA, siRNA, shRNA, miRNA, mtDNA, DNA/RNA hybrids, nucleic acid/polypeptide hybrid molecules, nucleic acids associated with exosomes or other extracellular vesicles, plasmids, viral DNA or RNA, viral vectors, and/or artificial chromosomes. In some embodiments, the nucleic acid encodes for a polypeptide to be expressed by the cell into which it is introduced.

In some embodiments, the exogenous agent is a single gene, open reading frame, or fragment. In some embodiments, the exogenous agent is multiple genes, open reading frames, or fragments.

In some embodiments, the systems, devices, and methods of the present disclosure introduce a polypeptide, mutant polypeptide, or fragment thereof into one or more cells. In some embodiments, the systems, devices, and methods of the present disclosure introduce a nucleic acid encoding a polypeptide, mutant polypeptide, or fragment thereof into one or more cells. In some embodiments, the polypeptide, mutant polypeptide, or fragment thereof is an enzyme, a ligand, a receptor, a structural protein, and/or a fusion protein. In some embodiments, the polypeptide is Apolipoprotein A-1 Milano. In some embodiments, the polypeptide is a corrected version of a mutated polypeptide in the cell. In some embodiments, the polypeptide is a mutated version of a polypeptide in the cell.

In some embodiments, the polypeptide is an antigenic polypeptide. In some embodiments, the antigenic polypeptide is from a bacteria, virus, parasite, or fungus. In some embodiments, the antigenic polypeptide is associated with a bacterial, viral, parasitic, or fungal infection.

In some embodiments, the antigenic peptide is associated with a hematologic malignancy. In some embodiments, the antigenic peptide is associated with a solid tumor. In some embodiments, the antigenic peptide is a tumor antigen (e.g. an antigen found only on a tumor cell). In some embodiments, the antigenic peptide is a tumor-associated antigen (e.g. an antigen found at a higher prevalence on a tumor cell than on a healthy cell). Ideally, the antigenic peptide is highly expressed on the surface of tumor cells but not expressed, or lowly expressed, on non-tumor cells. In some embodiments, the antigenic peptide includes, but is not limited to, 5T4, CA-9, transmembrane 4 superfamily (TM4SF) antigens, MART-1 (Melanoma Antigen Recognized by T cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a(1S), LAGE-1b(1L), NY-ESO-1), SSX (SSX1-SSX-5), BAGE, SCP-1, PRAME (MAPE), SART-1, SART-3, CTpll, TSP50, CT9/BRDT, gplOO, MART-1, TRP-1, TRP-2, MELAN-A/MART-1, Carcinoembryonic antigen (CEA), prostate-specific antigen (PSA), Tyrosinase, PD-L1, PD-1, HER2, VEGF, EGFR, CTLA-4, CD20, CD52, CD33, CD30, CEA, BCMA, MUC-1, HER2, VEGF, EGFR, EGFRvIII, ErbB, GD2, Glypican 3, mesothelin, NKGD2 ligands, BCM, IL13Ra2, CTLA-4, CD20, CD22, CD52, CD33, CD30, CD138, CD171, and/or CD19.

In some embodiments, the exogenous agent includes, but is not limited to, an antigen-binding moiety of a ligand, a receptor, or fragment thereof. In some embodiments, the exogenous agent includes a receptor-ligand fusion.

In some embodiments, the exogenous agent is an antibody or fragment thereof. Antibodies or fragments thereof include, but are not limited to, monoclonal antibodies, polyclonal antibodies, chimeric antibodies, humanized antibodies, murine antibodies, whole antibodies and/or any antigen binding fragment (e.g., an antigen-binding portion) and/or single chains of these (e.g. an antibody comprising at least two heavy (H) chains and two light (L) chains interconnected by disulfide bonds, an Fab fragment, a monovalent fragment consisting of the VL, VH, CL and CH1 domains; a F(ab)2 fragment, a bivalent fragment including two Fab fragments linked by a disulfide bridge at the hinge region; a Fd fragment consisting of the VH and CH1 domains; a Fv fragment consisting of the VL and VH domains of a single arm of an antibody; and the like).

In some embodiments, the antibody or fragment thereof is a therapeutic antibody known in the art. In some embodiments, the antibody or fragment thereof includes, but is not limited to, an anti-CD33 antibody, a HER2 antibody (e.g. trastuzumab), infliximab, adalimumab, belimumab, basiliximab, daclizumab, omalizumab, ramucirumab, alemtuzumab, benralizumab, bevacizumab, bimekizumab, cantuzumab, codrituzumab, dalotuzumab, efalizumab, elotuzumab, enavatuzumab, enokizumab, etrolizumab, farletuzumab, ficlatuzumab, imgatuzumab, itolizumab, lifastuzumab, ligelizumab, lodelcizumab, lorvotuzumab, mogamulizumab, motavizumab, obinutuzumab, ocaratuzumab, omalizumab, parsatuzumab, pateclizumab, perakizumab, pertuzumab, pidilizumab, quilizumab, rontalizumab, sofituzumab, solanezumab, suvizumab, teplizumab, tildrakizumab, tocilizumab, trastuzumab, trastuzumab emtansine, tregalizumab, vedolizumab, vorsetuzumab, vorsetuzumab mafodotin, yttrium (90 Y) clivatuzumab tetraxetan, anrukinzumab, dacetuzumab, daclizumab, etaracizumab, milatuzumab, ozanezumab, pinatuzumab vedotin, polatuzumab vedotin, tigatuzumab, veltuzumab, abituzumab, bococizumab, demcizumab, gevokizumab, ponezumab, ralpancizumab, romosozumab, tanezumab, blosozumab, concizumab, crenezumab, ibalizumab, ixekizumab, lebrikizumab, olokizumab, pembrolizumab, simtuzumab, ulocuplumab, vatelizumab, and/or samalizumab.

In some embodiments, the systems, devices, and methods of the present disclosure introduce a conjugated drug or molecule into one or more cells. Many such conjugated drugs or molecules are known in the art, and include, but are not limited to radioimmunotherapy (RIT), antibody-directed enzyme prodrug therapy (ADEPT), and/or antibody-drug conjugates (e.g. gemtuzumab).

In some embodiments, the systems, devices, and methods of the present disclosure introduce a drug into one or more cells. Drugs that can be used with the methods of the present disclosure include, but are not limited to, chemotherapeutic drugs, pro-apoptotic drugs, biologics, antibiotics, anti-fungals, ACE inhibitors, steroids, immunosuppresants, immunostimulants, immunomodulators, anti-inflammatories, and/or anti-fibrotic drugs.

Chemotherapeutic drugs that can be used in the systems, devices, and methods of the present disclosure include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2′,2″-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR inhibitor (e.g., erlotinib (Tarceva)) and VEGF-A that reduce cell proliferation, velcade, and pharmaceutically acceptable salts, acids or derivatives of any of the above.

Diseases and Disorders

Any appropriate disease or disorder may be prevented, treated, delayed, and/or ameliorated using the systems, devices, and methods of the present disclosure. In some embodiments, the disease or disorder is a cancer. In some embodiments, the disease or disorder is an infection (e.g. bacterial, viral, parasitic, and/or fungal). In some embodiments, the disease or disorder is associated with an infection. In some embodiments, the disease or disorder is a hereditary disorder. In some embodiments, the disease or disorder is environmentally influenced.

In some embodiments, the disease or disorder includes, but is not limited to, cancer, type 1 diabetes, type 2 diabetes, Alzheimer's disease, muscular dystrophy, cystic fibrosis, inflammatory diseases, atherosclerosis, fibrosis, Parkinson's disease, Multiple Systems Atrophy or Lewy Body Dementia, Amyotrophic Lateral Sclerosis, phenylketournia, Batten Disease or neuronal ceroid lipofuscinoses, Sanfilippo Syndrome, nephropathic cystinosis and Mucopolysaccharidoses diseases, achondroplasia autoimmune diseases, blood-borne diseases, sickle cell anemia, hemophilia, protein deficiency, vitamin deficiency, muscular disorders, nervous system disorders, paralysis, muscular atrophy, muscular degradation, Huntington's disease, Fragile X, Severe Combined Immunodeficiency Disorder (SCID), Tay-Sachs, Jackson-Weiss Syndrome, Ectrodactyly, dwarfism, Neurofibromatosis, Thalassemias, familial hypercholesterolemia, malaria, hormone deficiency, tuberculosis, Gram-positive infection, Gram-negative infection, viral infection, secretion of phage enzymes, secretion of endolysins, and/or vitamin deficiency.

In some embodiments, the disease or disorder has already presented with symptoms. In some embodiments, the disease or disorder is predicted to develop.

Administration

The exogenous agents can be administered in any appropriate dose and/or frequency to elicit an effect. In some embodiments, the methods of the present disclosure are repeated two, three, four, five, six, seven, eight, nine, ten, twenty, forty, or more times. In some embodiments, the methods of the present disclosure are repeated daily, weekly, monthly, bi-monthly, every other month, twice a year, yearly, every two years, every five years, every ten years, or more. In some embodiments, the methods of the present disclosure are repeated indefinitely.

In some embodiments, the methods disclosed herein are administered until symptoms are improved, prevented, delayed, or ameliorated. In some embodiments, the methods disclosed herein continue to be administered after symptoms are treated, prevented, delayed, or ameliorated.

Example 1

A sample/target was placed in a vacutainer within a magnetic field generated by a source of pulsed/transient magnetic field, which was a single layer solenoid wound over the vacutainer. The vacutainer contained whole blood with varying concentrations of DNA. The driving coil was pulsed a number of times, with different samples being exposed to varying levels of peak field by varying the charge voltage. Specifically, every sample was exposed to 50 pulses, and the driving voltage was varied for each sample, where variations in the driving voltage simultaneously varied the induced voltage and peak current.

Figure 7:
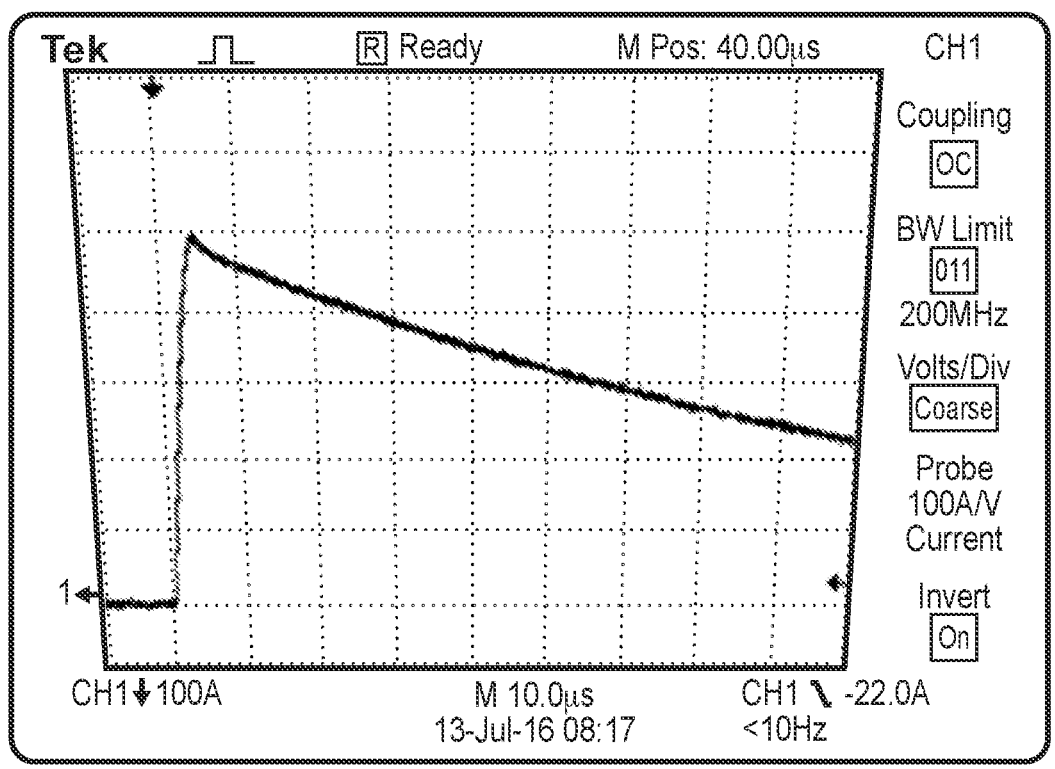
FIG. 7 illustrates an example electrical waveform, according to embodiments.

The quarter cycle current rise (see FIG. 7) for the waveform within the solenoid was ¼ sine wave. Then, the current was predominantly trapped in the inductive elements of the driving circuit (with a lingering amount of current trapped in the sample, which decay at a more rapid rate), therefore the predominantly LC ¼ rise transitioned to an L/R decay after the peak current was reached. The driving circuit included a fixed value capacitance, a switching component, and an essentially fixed inductance value; said another way, a switched LRC circuit was formed that was dominated by the "L" of the driving coil and the "C" of the capacitance). As a result, the period or frequency of the pulse was fixed. Accordingly, by varying the charge voltage of the driving circuit, the peak magnetic [B] field was varied. Since the frequency of the driving waveform was fixed, the dB/dT was also varied because varying peak fields were reached in a fixed time, which in turn varied the loop voltage and current density within the sample/target since the peak currents were higher at higher charge voltages. Current density, in addition to voltage within the sample, may affect efficacy, and this is illustrative of the interplay between the various aspects described herein. A driver that can vary the waveform that is applied to the target, or a driver with interchangeable drive coils, can be alternately employed.

An example of a magnetoporation test protocol is provided below.

Reagents:

DNA (240 µg nano-CMV-GFP); EDTA tubes and needles; Round bottom 10 mL plastic tubes; B cell culture media; PBMCs to use and isolate; small scale B cell isolation reagents; P3 buffer substitute (similar to P3 buffer sold by the Lonza group).

Coil Current Calculations:

The current in a 21-turn coil increases with increasing pulse strength. As also illustrated in Table 1, the sample current also increases with increase in =coil current.

TABLE 1

| Pulse strength (V) | | |
| --- | --- | --- |
| 250 | 700 | 974 |

Current in coil (A)

175 <-- in 21 T coil during 250 V pulse
500 <-- in 21 T coil during 700 V pulse
750 <-- in 21 T coil during 974 V pulse
Current in samples (A)

| | |
| --- | --- |
| 3675 <-- in sample during 250 V pulse with 21 T coil | 21 |
| 10500 <-- in sample during 700 V pulse with 21 T coil | |
| 15750 <-- in sample during 974 V pulse with 21 T coil | |

Construct:

Nano-CMV-GFP at 1 µg/µL: The target concentration of the DNA based on the first run is 20 µg/mL, and is tested according to the conditions in Table 2.

Whole Blood Protocol:

For conditions 1-12 (whole blood as the target substrate) the blood is drawn into an EDTA tube per standard phlebotomy protocol. The blood is aliquoted into 10 mL round bottom plastic tubes (2 mL/tube). The cells are magnetoporated and the whole blood is left as-is at 4° C. until PBMCs can be isolated via leucosep (ideally this is performed later in the same day, but it can be performed after overnight incubation). The cells are cultured for 2 days in standard B cell culture media, and GFP expression is checked under fluorescent microscopy on both days using the reagents listed in Table 3. On both days, the cells are counted with live/dead stain. The cells are analyze via flow cytometry. If unable to analyze immediately, freeze down at D2 per standard protocol. For 1 mL blood containing $5 \times 10^9$ RBC and $8.33 \times 10^6$ PBMC the yield will be about $1 \times 10^6$ cells.

Cell Suspensions:

For conditions 13-18 (cell suspensions as the target substrate), the PBMCs are thawed and $4 \times 10^7$ cells are immediately suspended in substitute P3 buffer. CD19+ B cells are isolated from the rest to yield $2 \times 10^7$ B cells and suspended in the same buffer. The cells are magnetoporated, and the cell suspensions are then resuspended in culture media as soon as possible after magnetoporation. The cells are cultured for 2 days in standard B cell culture media, and GFP expression is checked under fluorescent microscopy on both days using the reagents listed in Table 3. On both days, the cells are counted with live/dead stain. The cells are analyzed via flow cytometry. If unable to analyze immediately, freeze down at D2 per standard protocol. For 1 mL blood containing $5 \times 10^9$ RBC and $8.33 \times 10^6$ PBMC the yield will be about $1 \times 10^6$ cells.

TABLE 2

MAGNETOPORATION TEST CONDITIONS (DONE IN DUPLICATE)

| Condition | Target substrate | Volume of substrate (mL) | Buffer | Number of Cells (expected) | DNA Concentration (µg/mL) | Amount of DNA (µg) | Pulse (V) (50 × 250 µsec) | Coil |
| --- | --- | --- | --- | --- | --- | --- | --- | --- |
| 1 | Whole blood (optimal Cond.) | 2 | Blood | 1E10 RBC + | 20 | 40 | 250 | 21T |
| 2 | Whole blood (optimal Cond.)(dup) | 2 | Blood | 1.6E7 PBMCs/ | 20 | 40 | 250 | 21T |
| 3 | Whole blood (lower DNA) | 2 | Blood | 2 ml blood | 10 | 20 | 250 | 21T |

TABLE 2-continued

MAGNETOPORATION TEST CONDITIONS (DONE IN DUPLICATE)

| Condition | Target substrate | Volume of substrate (mL) | Buffer | Number of Cells (expected) | DNA Concentration (μg/mL) | Amount of DNA (μg) | Pulse (V) (50 × 250 μsec) | Coil |
|---|---|---|---|---|---|---|---|---|
| 4 | Whole blood (lower DNA)(dup) | 2 | Blood | (yield of PBMCs will be 2E6-4E6 after purification) | 10 | 20 | 250 | 21T |
| 5 | Whole blood (more DNA) | 2 | Blood | | 40 | 80 | 250 | 21T |
| 6 | Whole blood (more DNA)(dup) | 2 | Blood | | 40 | 80 | 250 | 21T |
| 7 | Whole blood (control) | 2 | Blood | | 0 | 0 | 250 | 21T |
| 8 | Whole blood (control)(dup) | 2 | Blood | | 0 | 0 | 250 | 21T |
| 9 | Whole blood (control)(2L-LV) | 2 | Blood | | 0 | 0 | 700 | 2L |
| 10 | Whole blood (control)(2L-LV)(dup) | 2 | Blood | | 0 | 0 | 700 | 2L |
| 11 | Whole blood (control)(2L-HV) | 2 | Blood | | 0 | 0 | 974 | 2L |
| 12 | Whole blood (control)(2L-HV)(dup) | 2 | Blood | | 0 | 0 | 974 | 2L |
| 13 | PBMCs | 2 | PBS + 50 mM glucose | 1.00E+07 | 20 | 40 | 250 | 21T |
| 14 | PBMCs (dup) | 2 | PBS + 50 mM glucose | 1.00E+07 | 20 | 40 | 250 | 21T |
| 15 | PBMCs (cell pellet in aliquot) | 0.2 | PBS + 50 mM glucose | 1.00E+07 | 20 | 4 | 250 | 1.5 |
| 16 | PBMCs (cell pellet in aliquot)(dup) | 0.2 | PBS + 50 mM glucose | 1.00E+07 | 20 | 4 | 250 | 1.5 |
| 17 | Isolated B cells (CD19+) | 0.2 | PBS + 50 mM glucose | 1.00E+07 | 20 | 4 | 250 | 1.5 |
| 18 | Isolated B cells (CD19+)(dup) | 0.2 | PBS + 50 mM glucose | 1.00E+07 | 20 | 4 | 250 | 1.5 |
| | mL of blood required --> | number of cells required --> 24 | | 6.00E+07 | | 376 | <-- total DNA required (μg) | |
| | Vacutainer draws required --> | 3 | | | | | | |

21T—21-turn coil (from first run. fits Vacutainer tubes)
2L—2-layer coil (similar to 21T, but with 2 layers and yields a much stronger field) was used in conditions 9-12
1.5—coil for 1.5 mL Eppendorf tubes The PBMCs and B cells in Table 2 are from the same donor (thawed the previous day).

TABLE 3

FLOW PANEL
Objectives: assess GFP expression, determine which cell population was transfected

| Target | Fluorphore |
|---|---|
| CD19 | CD19 vioblue |
| CD20 | CD20-APC-Cy7 |
| CD38 | CD38 PE-CY7 |
| CD3 | CD3-APC |
| CD56 | CD56-PE |
| FITC | GFP |

Figure 8:
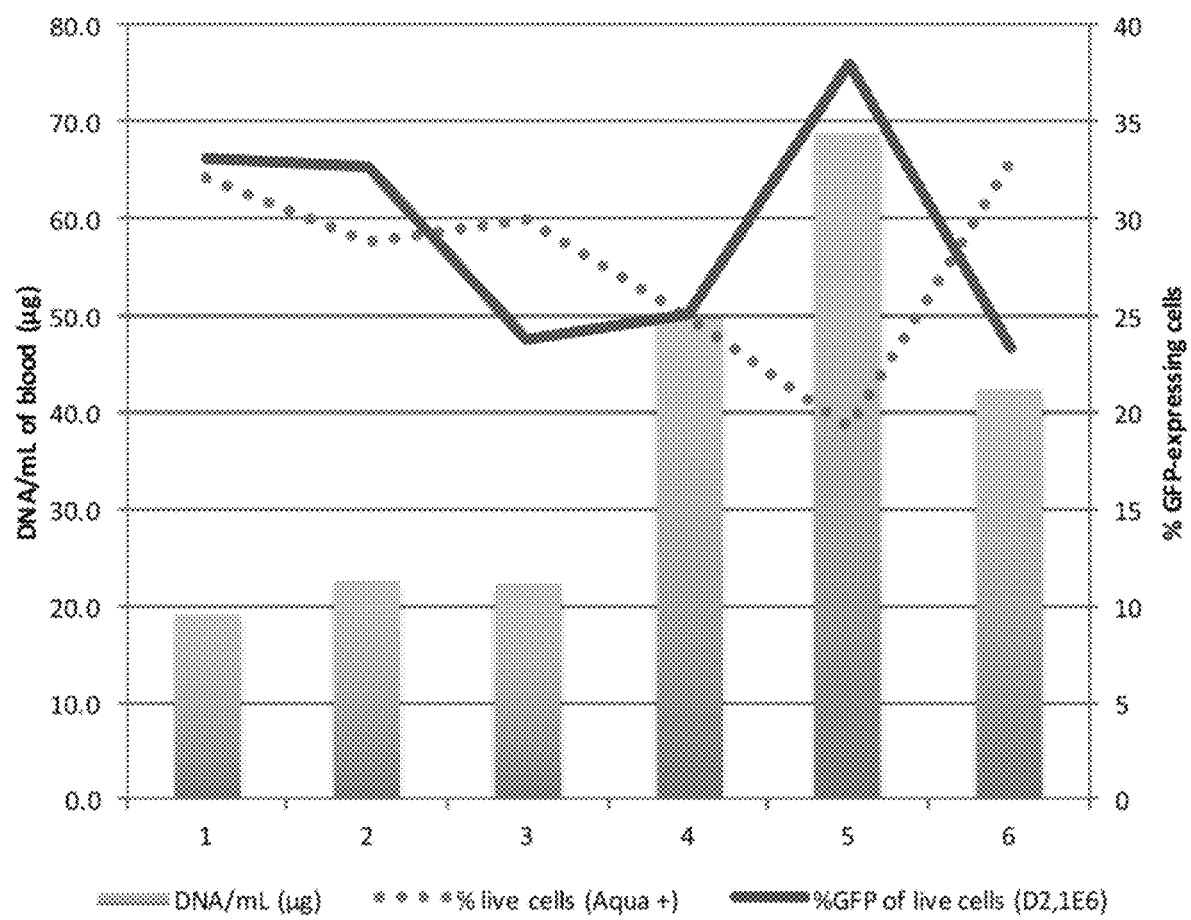
FIG. 8 shows a relationship between the DNA concentration in the blood cells after magnetoporation and transformation efficiency. All bars depict pulse strength in terms of voltage applied to a magnetic coil, with bars 1, 4=250V; bars 2, 5=700V; and bars 3, 6=974V.

The results of the above protocol are shown in Tables 4-6 below and in FIG. 8. Briefly, as observed with electroporation, there is a balance between DNA concentration, efficiency and cell death, and with Table 4 indicating DNA concentration needed for different levels of cell recovery. For both whole blood and cell suspensions, the highest pulse strength resulted in a drop in GFP expression. Further, higher DNA concentrations tend to lead to higher cell death, although this may not be true at the highest pulse strength, and may be due to lower loading efficiency at this strength. The optimal conditions here are 250V pulse with 20 μg/mL of DNA.

To test whether these methods have a preference for a particular cell type, or are uniform across cell types, plasmablasts will be tested using the methods taught herein.

TABLE 4

| | Viability | Cells recovered | Needed for for 5e5 | Needed for for 1e6 |
|---|---|---|---|---|
| 1 | 98.6 | 3.18E+06 | 0.314 | 0.629 |
| 2 | 95.9 | 3.27E+06 | 0.306 | 0.612 |
| 3 | 97.2 | 2.49E+06 | 0.402 | 0.803 |
| 4 | 96 | 2.33E+06 | 0.429 | 0.858 |
| 5 | 96 | 1.81E+06 | 0.552 | 1.105 |
| 6 | 93.7 | 2.45E+06 | 0.408 | 0.816 |

TABLE 5

| | original volume | cells/ml recovered |
|---|---|---|
| 1 | 5.2 | 3.06E+06 |
| 2 | 4.4 | 3.72E+06 |
| 3 | 4.5 | 2.77E+06 |
| 4 | 4 | 2.91E+06 |
| 5 | 2.91 | 3.11E+06 |
| 6 | 4.7 | 2.61E+06 |

TABLE 6

SUMMARY

| | DNA (μL) | Pulse strength (V for 50 pulses) | DNA/mL (μg) | DNA/cell (μg) | % live cells (Aqua+) | % GFP of live cells (D2, 1E6) |
|---|---|---|---|---|---|---|
| 1 | 100 | 250 | 19.2 | 3.27E−05 | 64.2 | 33.1 |
| 2 | 100 | 700 | 22.7 | 2.69E−05 | 57.7 | 32.7 |
| 3 | 100 | 974 | 22.2 | 3.61E−05 | 60 | 23.8 |

TABLE 6-continued

SUMMARY

| | DNA (µL) | Pulse strength (V for 50 pulses) | DNA/mL (µg) | DNA/cell (µg) | % live cells (Aqua+) | % GFP of live cells (D2, 1E6) |
|---|---|---|---|---|---|---|
| 4 | 200 | 250 | 50.0 | 6.87E−05 | 50 | 25.1 |
| 5 | 200 | 700 | 68.7 | 6.43E−05 | 38.3 | 38 |
| 6 | 200 | 974 | 42.6 | 7.67E−05 | 65.8 | 23.3 |

The pulses shown in Table 6 represent exponential decay. Rows 1-3 in Table 6 used a 21 turn coil, while rows 4-6 used 11 turn coils.

Example 2

In typical transfection protocols, only 1-2% of cells are transfected, and these display weak GFP expression. Methods disclosed herein using an inductor/saturable core disposed within the sample increased transfection efficiency to over 5% with cells displaying strong GFP expression.

Magnetoporation Protocol for HEK Cells (Saturable Core not Used):

HEK cells were magnetoporated (i.e., exposed to a transient magnetic field as disclosed herein) and checked 72 hours afterward. There were more GFP-positive cells observed in those exposed to 50 pulses, MEM condition. These cells displayed varied GFP expression, with some cells displaying weaker GFP expression then others. At the higher pulse conditions, viable cells were observed, but at a low amount. Cells subjected to the 1×PBS and hyperosmotic conditions displayed some GFP expression, but this was not higher than that observed in cells subjected to 1% MEM, >1×PBS, and >Hyperosmotic buffer.

Magnetoporation Protocol for HEK Cells (Saturable Core Used):

HEK cells were magnetoporated using an inductor/saturable core in the arrangement shown in FIG. 10. The experiment was run with the capacitors in the driving circuit being charged to about 4.0 kV. The cells were checked 24 hours after magnetoporation. Depending on experimental conditions, cells showed bright GFP expression with 1-5% transfection efficiency, with one group having 5% GFP positive cells. These conditions also displayed low cell death.

Example 3

In an example protocol, a treatment target/volume had a substantially cylindrical geometry with an outer diameter of about 9.5 mm, an inner diameter of 6.2 mm, a treatment volume of about 200 µl, and a height corresponding to the treatment volume. The sample in the treatment target included HEK cells exposed to GFP. The sample was exposed to a magnetic field having a dB/dt of from about 0.1 Tesla/µs to about 30 Tesla/µs. The electric field induced in the sample had a strength of from about 0.1 kV/cm to about 10 kV/cm.

The systems, devices, and methods of the present disclosure can be used in combination with any appropriate therapies known in the art. In some embodiments, the combination therapy is an anti-cancer therapy such as a chemotherapeutic agent, radiation, and/or surgery. In some embodiments, the combination therapy is an antibiotic, an antifungal, an anti-inflammatory, an antibody, a biologic, or vaccine.

Any of the embodiments described herein can include components that are manufactured, packaged, and sold independently or collectively. For example, in some instances, any of the components in the various embodiments described herein can be manufactured, assembled, and packaged collectively during a manufacturing process. In such instances, the package can be sold and/or otherwise provided as a kit.

Some instances described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other instances described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, instances may be implemented using Java, C++, .NET, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

The invention claimed is:

1. A system, comprising:
a control device including a set of independent circuits;
a set of magnetic devices coupled to the control device, the set of magnetic devices configured to magnetically or inductively couple to a treatment target including one or more cells exposed to an agent, each magnetic device of the set of magnetic devices including one or more magnetic coils and being independently addressable by a corresponding circuit of the set of independent circuits; and
a user interface configured to receive an indication of spatial information associated with an application of a set of transient magnetic fields,
the control device and the set of magnetic devices collectively configured to generate and apply the set of transient magnetic fields based on the indication of spatial information to the treatment target to porate the one or more cells and to permit the agent to enter the one or more cells.

2. The system of claim 1, the set of transient magnetic fields configured to induce an electric field in the treatment target to porate the one or more cells,
wherein the one or more magnetic coils of the set of magnetic devices are configured in proximity to at least a portion of the treatment target during use.

3. The system of claim 1, the control device including a signal generator configured to apply an electrical signal to each magnetic device of the set of magnetic devices,
the signal generator selected from the group consisting of an oscillator, a frequency synthesizer, a sine-wave generator, a pulse generator, a random noise generator, an arbitrary waveform generator, and combinations thereof,
the electrical signal selected from the group consisting of a pulsed ¼ sine wave, followed by an L/R decay, a sine wave, a decaying sine wave, a square wave, and an arbitrary waveform.

4. The system of claim 1, wherein each magnetic device of the set of0 magnetic devices includes: a ferromagnetic circuit element as an inductor, or a superconducting electromagnet configured to generate a transient magnetic field of the set of transient magnetic fields.

5. The system of claim 1, wherein the one or more magnetic coils of the set of magnetic devices are one or more oscillating antennae,
wherein each oscillating antenna of the one or more oscillating antennae is independently addressable.

6. The system of claim 1, wherein the set of transient magnetic fields defines a treatment volume of at least about 10 µL.

7. The system of claim 1, wherein the set of transient magnetic fields is configured to reversibly or irreversibly porate the one or more cells to permit the agent to enter the one or more cells.

8. The system of claim 1, wherein the treatment target includes at least one of: a container, a medical device, or a mammalian target,
wherein the one or more cells are in vitro, in vivo, or ex vivo.

9. The system of claim 1, wherein the one or more cells include at least one of:
mammalian cells selected from the group consisting of heart cells, liver cells, kidney cells, skin cells, brain cells, bladder cells, testes cells, ovary cells, uterus cells, eye cells, pancreatic cells, fallopian tube cells, vaginal cells, teste cells, prostate cells, placenta cells, large intestine cells, small intestine cells, colon cells, cancer cells, muscle cells, epithelial cells, connective tissue cells, nerve cells, blood cells, white blood cells, red blood cells, T cells, B cells, lymphocytes, antigen presenting cells, platelets, macrophages, monocytes, granulocytes neutrophils, eosinophils, basophils, and cancer cells;
bacterial cells;
fungal cells;
parasite cells; or
plant cells.

10. The system of claim 1, wherein the agent is a nucleic acid.

11. The system of claim 1, wherein the agent is a polypeptide,
wherein the polypeptide is selected from the group consisting of an enzyme, a ligand, a receptor, a structural protein, a fusion protein, an antigenic polypeptide, an antigen-binding moiety, a ligand-receptor fusion, an antibody, and a fragment thereof.
wherein the antigenic polypeptide is from a mammalian cell, a bacteria, virus, parasite, or fungus,
wherein the antibody or fragment thereof is selected from the group consisting of a monoclonal antibody, polyclonal antibody, chimeric antibody, humanized antibody, scFv, VL, VH, CL, CH1 domain, F(ab)2 fragment, a bivalent antibody, a Fd fragment, or a Fv fragment.

12. The system of claim 1, wherein the agent is a conjugated drug or molecule that is radioimmunotherapy (RIT), antibody-directed enzyme prodrug therapy (ADEPT) or an antibody-drug conjugate.

13. The system of claim 1, wherein the agent is a small molecule drug.

14. A method, comprising:
exposing one or more cells in a treatment target to an agent;
receiving an indication of spatial information associated with an application of a set of transient magnetic field; and
applying the set of transient magnetic fields to the treatment target based on the indication of spatial information to porate the one or more cells and to permit the agent to enter the one or more cells.

15. The method of claim 14, the transient magnetic fields configured to induce an electric field in the treatment target to porate the one or more cells.

16. The method of claim 14, further comprising generating the set of transient magnetic fields by applying an electrical signal to a magnetic device that is inductively coupled to the treatment target.

* * * * *